US005589047A

United States Patent [19]

Coster et al.

[11] Patent Number: 5,589,047
[45] Date of Patent: Dec. 31, 1996

[54] METHODS FOR THE SELECTION, SEPARATION AND FUSION OF CELLS

[75] Inventors: Hans G. L. Coster, Randwick; Robert G. Ashcroft, Sandringham; Tohsak Mahaworasilpa, Randwick, all of Australia

[73] Assignee: Fucell Pty Limited, Randwick, Australia

[21] Appl. No.: 204,253

[22] PCT Filed: Sep. 4, 1992

[86] PCT No.: PCT/AU92/00473

§ 371 Date: Apr. 5, 1994

§ 102(e) Date: Apr. 5, 1994

[87] PCT Pub. No.: WO93/05166

PCT Pub. Date: Mar. 18, 1993

[30] Foreign Application Priority Data

Sep. 5, 1991 [AU] Australia .................................. PK8213

[51] Int. Cl.⁶ .................................................... C25B 7/00
[52] U.S. Cl. ........................ 204/450; 204/547; 204/554; 435/173.4; 435/173.5; 435/173.6
[58] Field of Search ............................... 204/180.1, 186, 204/183.1, 299 R; 435/173.4, 173.5, 173.6

[56] References Cited

U.S. PATENT DOCUMENTS

| | | | |
|---|---|---|---|
| 4,018,662 | 4/1977 | Ruhenstroth-Bauer et al. | 204/299 R |
| 4,441,972 | 4/1984 | Pohl | 204/180 R |
| 4,561,961 | 12/1985 | Hofmann | 204/299 R |
| 4,970,154 | 11/1990 | Chang | 435/172.2 |
| 5,001,056 | 3/1991 | Snyder et al. | 435/173.6 |

OTHER PUBLICATIONS

Petrucci, General Chemistry: Principles and Modern Applications, 4th ed., p. 621, 1985 (no month).

Zimmermann et al., Electric Field–Induced Cell-to-Cell Fusion, The Journal of Membrane Biology, vol. 67, pp. 165–182 (1982) [no month].

*Primary Examiner*—John Niebling
*Assistant Examiner*—Edna Wong
*Attorney, Agent, or Firm*—Lee, Mann, Smith, McWilliams, Sweeney & Ohlson

[57] ABSTRACT

Methods are described for the separation of cells of different types using dielectrophoresis; for the electrochemical selection of cells by the dielectrophoretic attraction of ligand bearing cells into contact with an electrode bearing a complimentary ligand; and for the fusion of an individually isolated cell with another cell or a vector using dielectrophoresis to manipulate the cells or the cell and the vector into juxtaposition so that they may be fused.

24 Claims, 13 Drawing Sheets

METHODS FOR THE SELECTION, SEPARATION AND FUSION OF CELLS

FIELD OF THE INVENTION

The present invention relates to a method for the selective recovery of one or more cells expressing or bearing a defined bio-synthesised target molecule (a ligand); a method for the separation of cells of different types; and, independently but concomitantly, to a method for fusing just two such individual cells or for fusing such a cell and a vector to form one single "fusate cell". The fusion method is particularly applicable to the making of hybridomas, that is, the mammalian hybrid cells which produce monoclonal antibodies, and to other mammalian cell and plant cell constructs.

PRIOR ART

Hybridomas are binary hybrid cells made from the fusion of antibody secreting normal cells, for example B lymphocyte cells, with immortal cells which are in practice mostly non-secretors of antibody, usually a myeloma cell line. The secreting cells can be obtained by various means from an immunised animal, whilst the tumour line is grown in culture. The effect and purpose of the fusions is to produce numbers of different immortal hybrid cells each of which retains the genes for and property of producing and secreting a defined bio-synthesised target molecule such as a monoclonal antibody, specific to just one epitope of the antigen used in the immunisation. Although the commonest method of hybridoma generation involves direct bulk fusion of cells of the two types, immortalised antibody secreting cells have been produced by more exotic and more hazardous methods, such as by fusion of human B cells in the presence of transforming virus particles; this approach was developed because the direct translation of the method developed for mice cells to the human cell case had been largely fruitless. Such immortalised cells are also called hybridomas, though the usage is loose, since unlike the normal cell-myeloma cell hybridomas, the exact aetiology of these transformed cells is unknown.

Current hybridoma production methods involve a series of distinct steps (the method detailed is that used for the mouse):

i) Extraction (often by splenectomy) of B lymphocyte cells from an animal previously immunised to the antigen for which an antibody is being sought. Some enrichment methods may be used, post collection, to enhance the relative proportion of B-lymphocytes in the total cell count.

ii) The lymphocytes are mixed with a suitable immortal cell line such as myeloma cells and fusion between cells in the mixture is promoted by:
   a) Chemical means—for example by addition of polyethylene glycol (PEG),
   b) A fusagenic virus, or
   c) Short exposure to intense electric fields. Sometimes a combination of these is used.

The short exposure to electrical fields leads to electroporation and electrofusion. These phenomena are described in, for instance, U.S. Pat. Nos. 4,441,972 and 4,832,814.

iii) Selection and culturing of those cells that have survived and have fused. The fusion process produces fused cells (Fusates) resulting from single and multiple fusions of myeloma-myeloma, lymphocyte-lymphocyte and myeloma-lymphocyte partners.

If a suitable immortal fusion partner cell is chosen the myeloma-myeloma fusates can be eliminated by culturing in a special growth medium, typically a normal medium supplemented with Hypoxanthine, Aminopterin and Thymidine, ("HAT") in which these fusates cannot survive.

Normal Lymphocyte-normal lymphocyte fusates survive, and at most undergo only a limited number of cell divisions.

Some of the myeloma-lymphocyte fusates may remain viable after extended culture; these are the hybridomas—but they may not necessarily be hybridomas of interest, in that they do not necessarily make the defined bio-synthesised target molecule.

iv) The hybridomas which survive are screened to ascertain their production of antibodies and in particular antibodies specific for the original antigen of interest. If this procedure, which can be long and laborious, reveals a "clonal" fusate which produces the required antibody, the cell can be grown in culture to manufacture "Monoclonal Antibodies" in quantity.

v) The genetic stability of the hybridoma must be tested by culturing and re-cloning over an extended period of time.

The methodology employed to immortalise B cells as hybridomas has also been used to immortalise other distinct normal cell types as cell lines which secrete some defined bio-synthesised target molecule (for example, the human and mouse Interleukins) or perform some function (for example T-cell effector function or phagocytic activities) of clinical or commercial interest.

Present methods of generating cells which secrete the desired products have defects and limitations (exemplified here for the case of hybridomas), specifically:

i) In a typical PEG-mediated fusion of 100 million spleen cells and 10 million myeloma cells, the yield of fused cells would be less than 1000, of which four or five cloned cells, but frequently none, make antibody of the desired specificity. This leads to the practice of doing 5–10 fusion operations at one time, resulting in laborious subsequent processing to find the suitable hybridoma.

The fusion probability can be improved by exposure of the cells to intense electric fields for very brief periods; this process is known as "Electroporation", for example see Reference 5 at the end of this specification. The fusion probability for cells in suspension, however, remains low, for example $1.5 \times 10^{-5}$, see US Pat. No. 4,832,814.

A higher success rate again has been achieved by using chemical agents to effect linkage and proximation of cell pairs of the desired type (that is, myeloma and B cell), in a suspension, prior to electric field exposure. The method has not found extensive use, perhaps because of its complexity, susceptibility to contamination or low efficacy. This is especially significant in cases where a molecule occurring at low incidence on a cell's surface is the antigen of interest in immunisation and fusion.

ii) The fusion process between the cells is indiscriminate. Lack of selection of the cells for fusion occurs at two levels of cell specification:
   a) Non-Hybrid Fusion
      The lack of discrimination of the process produces:
         Lymphocyte-lymphocyte fusates
         Myeloma-myeloma fusates
         Lymphocyte-myeloma fusates: these are the only hybrid fusates, and the only fusates of value.
   b) Non-selective Hybrid Fusion
      Those lymphocyte-myeloma fusates which are produced, are produced indiscriminately.

There is no selection mechanism to allow only those lymphocytes which are producing the antibody of interest to fuse with myeloma cells; those hybridomas must be isolated some weeks afterwards, following outgrowth of the heterogeneous cell fusion mixture.

iii) The current method requires five separate post-fusion selection procedures which carry risks of hybridoma loss due to contamination or failure of selection methods: HAT selection (includes over seven days of feeding cultures), isolation of antibody secretors, cloning, assay for specific antibody and final cloning.

HAT selection is only effective if the myeloma cell line is HAT sensitive and this greatly limits the choice of fusion partner cells in the current methods. This has proven to be a major obstacle in the development of human hybridomas by the traditional methods.

The electrofusion method referred to earlier actually involves three phenomena. The first of these is the phenomenon of dielectrophoresis which describes the movement of cells when they are exposed to a non-uniform, radio frequency electric field. This phenomenon has been described in detail in the monograph by Pohl (ref 1). The non uniform electric fields are usually produced by the application of radio frequency signals to electrodes shaped for instance as cylindrical wires to create non-uniform fields and the work of Pohl (ref 1 and U.S. Pat. No. 4,441,972) has taught that the cells are attracted towards the regions where the field is most intense for wire electrodes that is towards the surface of such electrodes. Pohl has also taught us that the dielectrophoresis of cells is strongly promoted by suspending the cells in solutions of low electrical conductivity. When radio frequency electric currents are passed through such solutions containing a suspension of a multitude (millions) of cells, the space around each cell becomes a region in which the electric field is non-uniform and increases as one approaches the surface of the cell. As Pohl (ref 1) and Zimmermann (ref 5) have taught us, this causes cells to align themselves in linear chains usually referred to as pearl chains. The second phenomenon involved in electrofusion is that of electrical breakdown of cell membranes. This process occurs when large but very short pulses of current are passed through a suspension of cells as taught by Sale and Hamilton (ref 6) and Zimmermann et al (U.S. Pat. No. 4,081,340) or in single cells as taught by Coster and Zimmerman (refs 2, 3 and 4). Such electrical breakdown of cell membranes also leads to an increased permeability, referred to as "electroporation", of the cell membrane as taught by Sale and Hamilton (ref 6) and Sepersu et al (ref 7) and Zimmermann et al (U.S. Pat. 4,081,340). The third phenomenon concerns the fusion of cells which can occur when the cells are first aligned in linear chains in an inhomogeneous electric field and then caused to undergo electrical breakdown as taught by Neumann et al (ref 8), Zimmermann et al (ref 9), Pohl (U.S. Pat. 4,476,004), Root (U.S. Pat. No. 4,832,814), Hoffman (U.S. Pat. No. 4,561,961) and Marshall (U.S. Pat. No. 4,906,576). The cells aligned in "pearl chains" by dielectrophoresis are drawn in random manner from the suspension of the cells and the subsequent multiple fusions occur between adjacent cells in the many "pearl chains" in a largely unpredictable manner throughout the collection of chains. The apparatuses and methods of the present invention improve upon the prior art of electrofusion by providing methods for selectively manipulating one cell (or vector) with particular attributes (for instance a secreting B lymphocyte) and another cell (or vector) with different attributes (for instance a myeloma cell), and bringing these two cells together as a single pair of cells, and fusing this single pair of cells and no other.

DISCLOSURE OF THE INVENTION

The present invention consists, in a first aspect, in a method for the selective recovery of cells, vectors, particles or molecules expressing or presenting a defined ligand, comprising the steps of attaching to the surface of a target a ligand or ligands complimentary to the defined ligand, introducing the target into a suspension or solution of cells, vectors, particles or molecules in an electrically conductive liquid in which some of the cells, vectors, particles or molecules express or present the defined ligand, causing at least some of the cells, vectors, particles or molecules expressing or presenting the defined ligand to migrate into contact with the target and to bind with the complimentary ligand or ligands by establishing between a pair of electrodes in the suspension or solution an alternating electric field of suitable frequency, intensity and inhomogeneity, and separating the cells, vectors, particles or molecules which have bound to the target from at least some of the other cells, vectors, particles or molecules in the suspension. This method is hereinafter termed "electrochemical selection".

The phenomenon of dielectrophoresis may be employed to transport cells, vectors, particles or molecules through a low conductance medium, such that they contact a target placed in their path, for instance an open mesh, sometimes having the opportunity to attach to complementary ligands on the target, and thus being bound to it or otherwise allowed to pass across or further through the target.

In preferred embodiments of the invention the target is in fact one of the electrodes which has been suitably coated with the complimentary ligand or ligands. Over certain ranges of frequencies, intensities and inhomogenieties of the electric field, cells can be repelled from the electrodes, and since this effect is dependent on cell type, it is possible to selectively retain subsets of a mixture of cells on the target, while repelling other subsets of cells from the target. The process of first attracting cells onto the first electrode can be assisted in some cases by the application of a steady electric field, and the alternating current (AC) electric field used to attach the cells should be of such frequency that the required cells will be attracted to the coated electrode, and since the force on the cells varies continuously but not monotonically with frequency and is dependent on cell type, it is possible to selectively cause the chosen cells to drift towards a particular electrode. The invention includes the subsequent capability of manipulating the attached cells by rotation or translation, so as to facilitate the fusion process.

In a second aspect the present invention consists in a method for the separation of cells, vectors, particles or molecules in a suspension or solution of cells, vectors, particles or molecules of at least two different types of those elements in an electrically conductive liquid, comprising the steps of establishing between two electrodes in the liquid an alternating electric field of such frequency, intensity and inhomogeneity as to selectively cause the cells, vectors, particles or molecules of one type to migrate through the liquid towards the electrodes while simultaneously or sequentially causing cells, vectors, particles or molecules of another type to migrate through the liquid away from the electrodes and separating those cells, vectors, particles or molecules which have migrated towards the electrodes from those that have migrated away from them.

In this aspect of the invention the alternating current will be maintained until some or all of the cells of the one type are in contact with at least one of the electrodes and the remaining cells are then removed from the electrodes such as by being flushed away.

In a third aspect the present invention consists in a method for fusing a selected first cell with a selected second cell or vector to form a single fusate cell, comprising the steps of isolating the selected first cell, bringing the selected first cell into juxtaposition with the second cell or vector and holding the cells or the cell and vector in juxtaposition by an alternating electric field of appropriate frequency, intensity and inhomogeneity, and causing the cells or the cell and the vector to fuse.

The cells to be fused may be prokaryotic or eukaryotic cells. In preferred embodiments of the invention they are mammalian cells and more importantly at least one of them could be a human cell. The method according to this invention may also be used to introduce a vector such as a plasmid, or an artificial construct containing useful DNA or RNA, be it a liposome, vesicle or modified prokaryote or eukaryote, into a cell. As used herein the term "vector" is taken to mean any carrier of DNA or RNA, whether naturally occurring or constructed, which allows the transfer of the DNA or RNA through the membrane of a cell.

The method according to the third aspect of the invention is particularly applicable to the fusing of a cell expressing a gene coding for a desired molecular species with an immortal cell. The desired molecular species may be an antibody, however, it could also be an enzyme, a growth factor, a necrosis factor or any other bio-synthesised ligand or biomolecule. The invention may also have other uses however. Two embryonic cells could be fused to produce a polyploid fusate, or two haploid cells, normal or otherwise, could be used to produce a new diploid fusate.

The method according to the first aspect, and in alternative embodiments is especially useful for processes which require the selection and manipulation of small numbers of cells including just one cell, in many tissue culture applications. It is also useable in such embodiments, with suitable electrode geometries, and/or by using a selective target not itself an electrode as a separator of mixtures of cells into their homogeneous sub-groups.

In preferred embodiments the present invention overcomes each of the problems associated with the prior art. The present method allows selection, apposition and pairwise fusion of living cells and cell-like vectors. The method according to preferred embodiments of this invention provides:

i) Selection, for fusion or for other purposes, for example of specific cell enrichment, of just those cells which are secreting Monoclonal Antibody molecules which are antigen specific, or secreting bio-synthesised molecules specific to the (bio)chemicals employed in the selection process (for types of cell hybrids other than the antibody secretors).

ii) Over 90% efficient, pair by pair, specific binary fusion of the cells binding the specific antigen—or other target molecule—with a selected fusion partner (a myeloma cell or other immortal cell).

iii) The opportunity to employ a cell from any desired cell line as a fusion partner for a normal, producing and/or secreting cell, without any requirement for nutrient sensitivity such as HAT, for the production of immortal binary hybrids of possible secretory or synthetic capability.

iv) Post fusion selection of stable secretors of specific bioproduct, achieved by using the first aspect of the present invention as a culling step to replace present post-fusion culture procedures. Some of the steps in the prior art production methods are eliminated.

The new method has many ramifications which provide new and unique opportunities in the application of monoclonal antibodies and other secretory cell products. The new method also makes possible the production of human monoclonal antibodies and other secretory cell products of human origin.

BRIEF DESCRIPTION OF THE DRAWINGS

Preferred aspects of the present invention will be hereinafter described with reference to the accompanying drawings in which:

FIG. 29 shows attraction of cells to selective electrodes;

FIG. 30 shows attachment by electric force allow chemical adhesion of some cells; and FIG. 31 shows repulsion of unbound cells from the electrodes.

BEST MODE FOR CARRYING OUT THE INVENTION

The invention is illustrated by the following procedure.

1. Method of Cell Selection for the Secreting Cells

The preferred embodiment of the cell selection process for use in fusions employs the force generated by direct and alternating electric fields of divers waveforms, intensities and frequencies developed between two or more electrodes, one or more of which may be bare or covered with an indifferent chemical, and another of which is coated with the antigen or other target molecule (ligand), adhesive to the target cells, so as to ensure the attachment of one or more of such cells for use in the fusion process. The frequencies of and gradients in these electric fields can be adjusted to achieve an optimal selection of the cell desired, since the strength and direction of the electric force depend on the frequency. The detailed variation of the force with frequency for the various cell and vector types depends upon the detailed membrane and internal structures and their organisation. This embodiment also uses the electric force and electromechanical manipulators to translate attached cells to the fusion site and to there configure them with partners, preliminary to their fusion.

Figure 1:
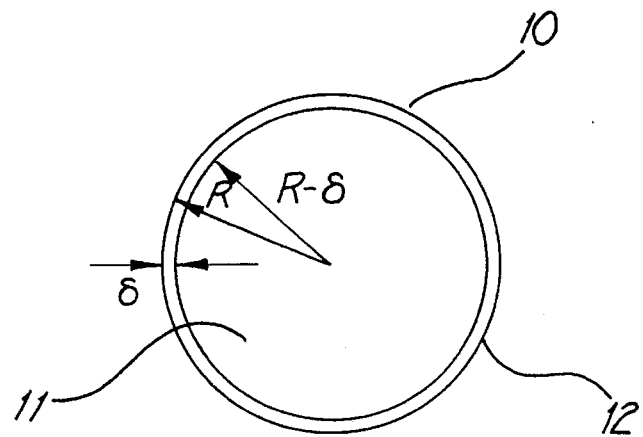
FIG. 1 is a simple model of a cell 10, in which a uniform interior of relatively high conductance and dielectric constant 11 is surrounded by a thin membrane of opposite attributes 12.
Figure 2:
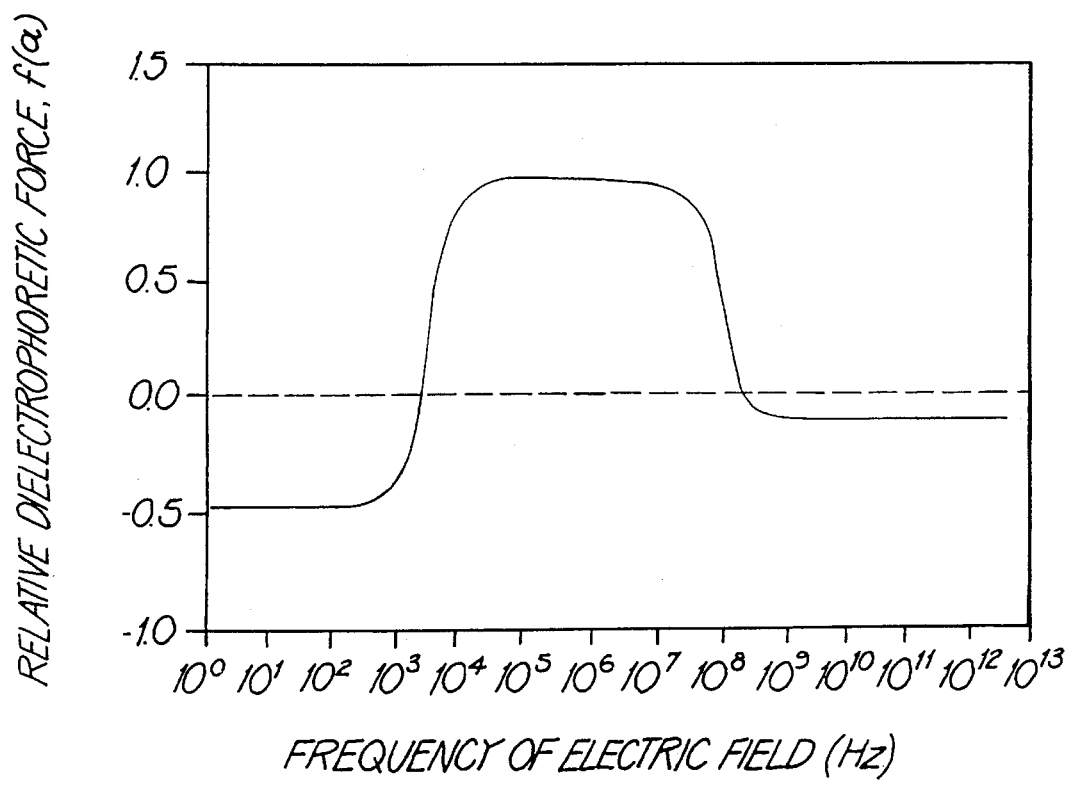
FIG. 2 is a typical example of the frequency-dependent component of the force curve as a function of frequency for a simple model of a cell, where the model cell itself is suspended in an aqueous solution of low conductivity.

As seen in FIG. 1 a cell 10, surrounded by a membrane 11, is suspended in an aqueous medium 12. The interior of the cell has a relatively high conductance and dielectric constant whereas the cell membrane 11 is of opposite attributes. The aqueous solution is of low conductivity. FIG. 2 shows the way in which dielectrophoretic force on the cell changes as the frequency of an alternating electric field is applied to the cell 10, the force is directly proportional to the gradient in the square of the intensity of the electric field ($\nabla E^2$) and the product of the function $f(\alpha)$ shown in the present figure; for actual living cells, the detailed variation of the force in an inhomogeneous field is modified by its detailed membrane and internal structures and organisation; this varies from one cell type to another; the curve shows the relative dielectrophoretic force as a function of AC field frequency for the following parameters, Permittivity of the membrane ($\epsilon_m$)=10$\epsilon_0$ Permittivity of the cytoplasm ($\epsilon_c$)=60$\epsilon_0$ Permittivity of the external medium ($\epsilon_s$)=80$\epsilon_0$ Conductivity of the cytoplasm ($\sigma_c$)=1.0 S.m$^{-1}$ Conductivity of the external medium ($\sigma_0$)=0.001 S.m$^{-1}$ Thickness of the cell membrane ($\delta$)=10 nm Radius of the cell (R)=10 μm, where $\epsilon_0$ is the permittivity of free space, =8.85×10$^{-12}$ F.m the dielectrophoretic force is given by F=2π$\epsilon_s$R$^3$($\nabla E^2$)f($\alpha$), where ($\nabla E^2$) is the gradient in the square of the electric field intensity and f($\alpha$) is the function shown in the figure;

The electric field between a pair of electrodes can be established by the application of an alternating current (AC) signal to those electrodes. The field at the surface of the electrodes, or at any point between them, can be calculated from the geometry (for instance diameters) of the electrodes and their location (for instance separation). In addition, it is necessary to determine the fraction of the applied AC signal that will appear across the solution and which fraction appears across the electrical double layer that forms at the electrode-solution interfaces. The fraction of the total applied potential appearing across the solution itself depends on the frequency of the AC potential, the ionic composition of the solution and the nature of the electrodes. The variation with frequency is due to a process known as "impedance dispersion" of the electrode-solution system. It should be noted that only the fraction of the field appearing across the solution contributes to the dielectrophoretic movement of the cells or vectors in the solution. The fraction of the potential appearing across the double layer, however, contributes to the molecular binding processes at the electrode-solution interface.

Other embodiments of the selection process require no coatings to be employed on some or all of the electrodes, since a previous formal selection process, for example fluorescence activated cell sorting, FACS, may have been employed to ensure that all or most of the cells or vectors introduced and then attached to the relevant electrode produce the desired biosynthesised target molecules. This would particularly apply where the target cells synthesise but do not display on their surface the biosynthetic defined ligand, as may occur with plasma cells, the terminally differentiated antibody producing cells in the B-cell lineage.

Figure 29:
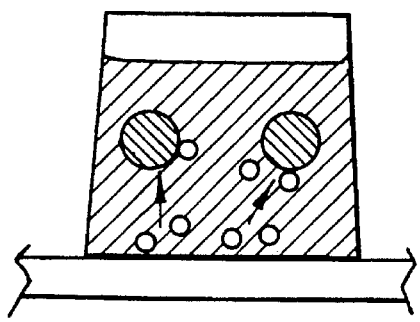
FIGS. 29 to 31 are schematic diagrams of the electrochemical selection procedure applied to cultured fusate cells, which have undergone several cell divisions; those cells which synthesise and express antibody can be isolated from cells which do not, by employing the antigen-coated electrode and another electrode, as described for the electrochemical selection of normal secreting cells prior to fusion.
Figure 30:
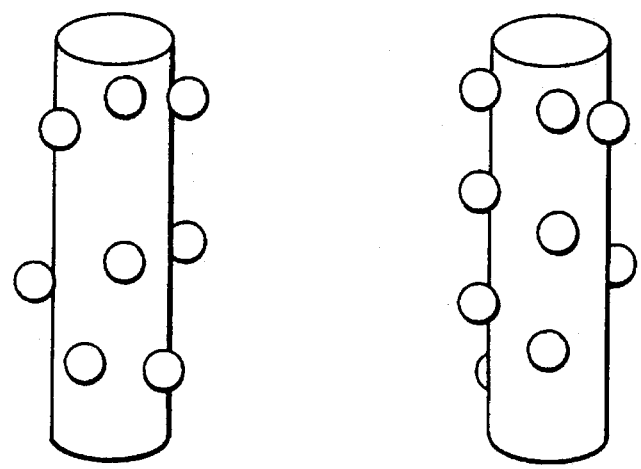
Figure 31:
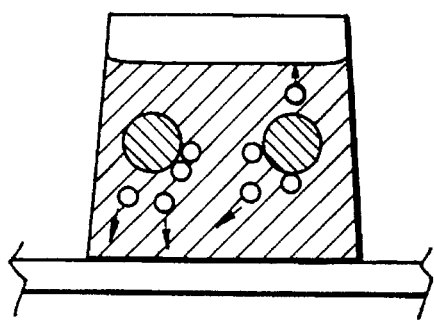

The preferred embodiment of the cell selection process for its use in selection of wanted hybrid cells growing in culture, for example following the period after a successful fusion, employs the electrochemical selection process at different stages of the selection cycle; this is exemplified in the Examples section of this specification, and is shown schematically in FIGS. 29, 30 and 31.

(a) Cell Selection

While it is preferred in the process of electrochemical selection that the ligand complimentary to the defined ligand is provided on at least one of the electrodes it is also possible to provide the ligand on another target, such as a plain porous polymer sheet on which complimentary ligand molecules are attached, provided that the movement of the cell into contact with the ligand bearing target is able to be induced by the alternating electric field. Such non-electrode targets may be useful to pre-enrich for cells expressing the defined ligand, from a large volume and/or number of indifferent cells.

Cells expressing the required antibody are selectively attached to an electrode in an aqueous solution or non-aqueous solution of benign tonicity and properties. The electrode is usually, but not necessarily, a cylindrical wire electrode.

It is usually efficacious to use cell suspensions in an aqueous medium of low conductivity for instance, an isotonic solution of sorbitol or glucose or other sugar. The reasons for the two main features are: aqueous, because this maintains cell viability well when properly employed and of low conductivity, to maximise the electric forces experienced by the cells when alternating currents are passed through the medium.

The operations require very small numbers of cells and very small volumes of solution and may be performed entirely on the stage of an optical microscope; the whole operation can then be monitored under the microscope.

i) Construction of the Cell-Selective Electrode

The electrode is coated with the antigen to which the secreting cells are producing antibodies or with another ligand to which cells make a defined bio-synthesised target molecule of interest, that is, the defined ligand.

The 'antigen' referred to here may in fact be whole cells which themselves are known to be expressing the antigen of interest, but for which the antigen molecules have not been isolated or cannot be obtained easily or at all in purified form. If the 'antigen' is a whole cell expressing the antigen of interest, the electrode is first covered with those cells. The latter can be achieved in several ways which are described in subsequent sections.

Figure 3:
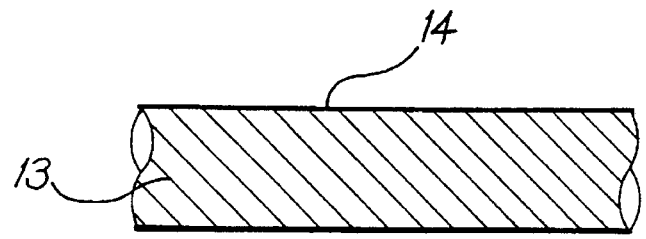
FIG. 3 is a diagrammatic representation of an electrode 13 coated with a targetted antigen 14, this electrode is an example of a chemically selective electrode.
Figure 4:
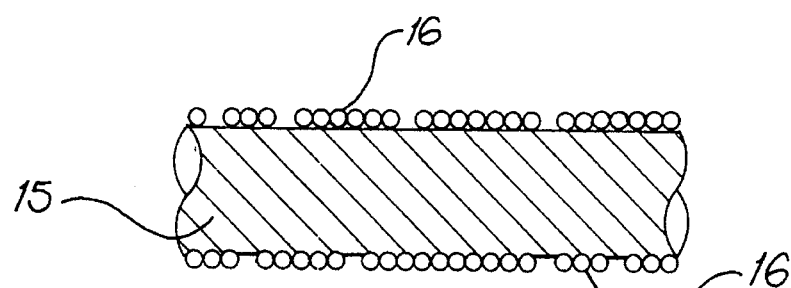
FIG. 4 is a diagrammatic representation of an electrode 15 coated with cells 16, non-specifically attached to the electrode, which are expressing the target antigen on their surfaces.
Figure 5:
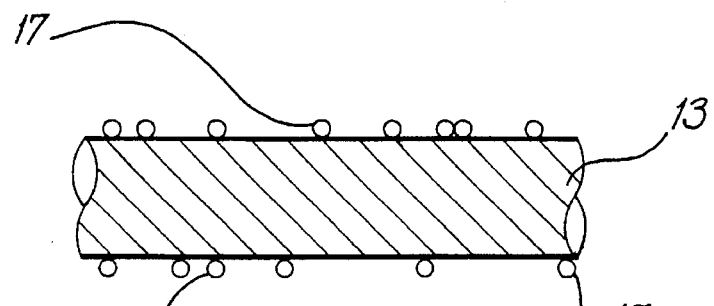
FIG. 5 is a diagrammatic representation of the electrode 13 of FIG. 3 to which several normal antibody secreting cells 17 have been attached using the method of electrochemical selection described herein.
Figure 6:
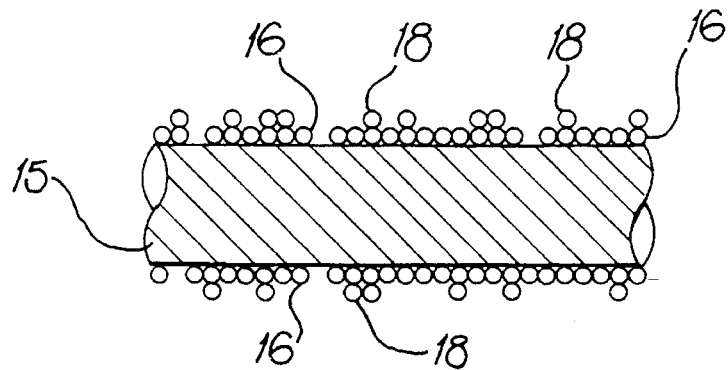
FIG. 6 is a diagrammatic representation of the electrode 15 of FIG. 4 to which a number of secreting (usually antibody secreting) cells 18 have been attached.

The coating of the electrode with the antigen is performed by immersing the electrode in a solution containing a suitable concentration of the antigen, as shown in FIG. 3. The coating process may be promoted by the application of an alternating and/or steady, electric field, of possibly varied polarities and for possibly varied time intervals, for example they may be pulsed at some stage of the coating cycle. Thus, by using a combination of AC fields of optimum, frequency, field strength, and field gradient and steady DC fields, it is possible by changing the polarity of the steady field, to attach the antigen or other ligand in different, preferred orientations on the electrode.

ii) Selective Electrodes Incorporating Antigen Expressing Cells

If the 'antigen' is not itself available in pure form or in its natural structure [for example when a protein is denatured by the purification process], except as it appears on a cell which itself is expressing the antigen molecules on its surface, the selective electrode can be coated with these cells by immersing the electrode in a suspension of the cells and applying an alternating electric field of suitable frequency (usually radio frequency) between the electrode and a remote indifferent electrode. The cells can then be attached to the electrode by electroselection, that is, the employment of a dielectrophoretic force to attract one or more cells up to an electrode. The process of selectively attaching the target cells can also be assisted in some cases by the application of a steady electric field. Once the 'antigen' cells cover the surface of the electrode they may be more permanently attached by the application of short (microsecond) electric pulses. Such pulses, if of the correct strength and duration, will cause molecules on the surface of the cells to become attached to the electrode. The choice of the most appropriate pulse strength and duration depends on the cell species. When so attached, these cells will remain on the electrode even when the alternating or steady electric field is removed. It is, however, not a necessary requirement for the method in principle, that the cells be so firmly attached.

iii) Selective Electrodes Incorporating Antibodies Derived from Another Species

In some cases it may be desired to use antigen expressing cells to coat the electrode, as described in section (ii) above, but a suspension consisting of only those particular cells cannot be readily produced. For many such antigens, monoclonal antibodies derived from a hybridoma of a different animal species, or polyclonal antibodies against the antigen, or molecular fragments of either types of antibodies may already be available. In this case the electrode should be first coated with that species' antibodies, or molecular fragments thereof, directed against the antigen expressed by the cells of interest (even though only a mixture of those cells with other cells is available). This coating of the electrode with the antibodies is performed as described previously in section (i) above. The antibody coated electrode is then used to select for, and then coat the electrode itself with, those cells which are expressing the antigen of interest. This process is described in the next section but here refers to coating the electrode with cells expressing the antigen, whilst the next section describes how such a "selective" electrode may then be further coated with cells secreting antibodies to the antigen.

iv) Pre-coating the Electrode or other target

In some cases it may be necessary to first coat the electrode or other target with a thin coating of a monomeric or polymeric substance, such as polyamide, protein A, avidin or other substance which provides a strongly, but not necessarily selective, absorbing surface. The electrode or other target itself may be constructed from conducting organic materials, for example, iodine doped polyacetylene, or polypyrrole, etc.

b) Coating the Electrode with the Normal, Secreting, Cells

Unbound cellular or molecular reagents (molecules, cells, vectors or other reagents)- remaining after the coating of the selective electrode, are removed from the chamber by any suitable means, typically by flushing with fresh solution. The molecular or cellular coating previously applied to the selective electrode remains fixed on that electrode, ready to ensure the attachment of the cells of interest.

A suspension of cells containing the secretory cells of interest, but not necessarily solely composed of these cells, is then introduced into the electrode chamber. This mixture of cells contains the normal cells, the producers of the bio-synthesised molecules of interest, which are to be fused with the immortal partner cells of the cell line or with appropriate vectors. Typically they would be freshly prepared lymphoid cells from peripheral blood or other suitable, available, organ (tonsil, spleen etc), often partially enriched using a selective target and dielectrophoresis and/ or by using standard cell preparative methods from hematology or by cell sorting, typically Fluorescence Activated Cell Sorting. In some applications they may be cultured cells, treated or untreated, normal or otherwise.

As stated above, it is possible by electrochemical selection to selectively attract and attach, then subsequently retain a subset of a mixture of cells on a chemically selective electrode, refer to FIGS. 29, 30 and 31. The process of first attracting cells onto the first electrode can be assisted in some cases by the application of a steady electric field, and the AC electric field used to bring up the cells needs to be of such frequency that the required cells will be attracted to the coated electrode and drift towards it. This electric field should also be of an intensity which is sufficiently low so that it does not lead to fusion of cells in close proximity to each other nor to electrical breakdown of the cells. It should gently force the suspended cells onto the chemically selective electrode, thus allowing the local specific chemical binding (and thus selection) to occur without causing a denaturing of protein molecules on the cell surface, which might otherwise cause cells to bind to the electrode in a non-specific manner. Following appropriate use of the repulsion mode of electrical selection, only those cells excreting the correct antibody complementary to the coating on the coated electrode, and thus bound to the electrode strongly enough, will remain attached.

Appropriate changes to the applied fields allow one to selectively retain only those cells expressing high affinity antibodies by applying electric forces that oppose the antibody-antigen binding process; the strength of this opposing electric force can be adjusted by adjusting the strength and direction of the steady electric field and by changes to the frequency and intensity of the AC field.

In an alternative embodiment, the selective electrode is made of a porous, electrically conductive material and the cells are drawn to the electrode by applying suction to one side of the electrode. The removal of unwanted cells can then be achieved by back-flushing or by the methods outlined above.

2. Selecting the Immortal Cell Fusion Partner

Any secretory cells left in suspension are removed by gently flushing with an aqueous solution, or by other methods as detailed above.

Figure 7:
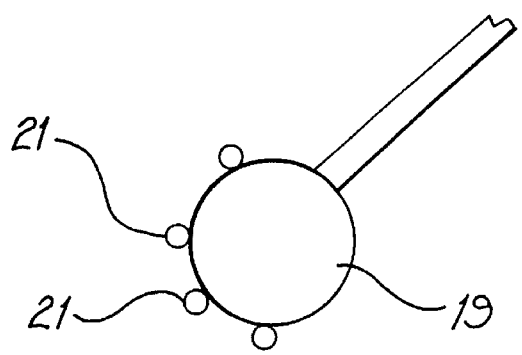
FIG. 7 is a diagrammatic representation of a further electrode 19 to which several immortal, partner cells 21 have been attached.

In the case of hybridoma generation, the immortal (for example myeloma) cells are now introduced into the same chamber or into an adjacent chamber, which may in some embodiments communicate with the first chamber via a channel also filled with the aqueous solution in which the cells are suspended. They can be made to adhere to another, uncoated (non- selective) or a coated chemically selective electrode which differentially binds this partner cell, by the application of an alternating and/or steady electric field applied between this electrode and another in the chamber. It is possible, by choice of a suitable electrode geometry, by appropriate controlling of field strength, waveform and intensity of the applied fields and by controlling the number of the immortal cells introduced into the chamber to restrict the number of cells attached to this electrode to any desired number (including a single cell), see FIG. 7.

The electrode to which the immortal cells are to be attached can be also, but not necessarily, first coated with a polymer, protein or other substance including an antigen or other ligand binding molecule specific to the immortal partner cells before the cells are attached as described above. This, in some instances, is advantageous as such a pre-coat might provide a more symmetrical electric field distribution since the normal cell on the antigen-primed selective electrode is also attached to a coated electrode. Pre-coating the electrode which is used for the immortal cells, however, was not always found to be necessary. In some instances it may be advantageous to deliberately create asymmetries in the field intensity gradients at the two electrodes. This can be achieved in some embodiments by coating the electrodes with layers of dielectric materials and/or using electrodes with different curvature or other geometric differences. This feature may be particularly useful in the cell transfer operation described below.

3. Appressing the Selected Pairs of Cells for their optimal fusagenic state

A critical step in producing the desired hybrid cell is to bring the two selected fusee cells together as a single pair of cells. This may be achieved in one of three preferred ways. In the first, the electrode bearing partner cells is held in a micromanipulator which allows the operator to bring this cell or cells, held by the electric field, into contact with the secretory cells attached to the cell selective electrode, thus bringing directly into pairwise contact (apposition) the selected secretory cell with the chosen immortal partner cell, see FIG. 8.

In the second way of bringing the fusee pair of cells together, (refer to FIGS. 20 through 24) the partner cell is transported by the transfer electrode, also held in a micromanipulator, and transferred from this electrode onto the secretory cell (itself attached to the selective electrode), by a combination of mechanical manipulation and changes (transient or otherwise) in the strength and/or frequency of the electric field, which causes the cell on this electrode, or a cell attached non-selectively to another cell on this electrode, to detach itself and migrate under the influence of the field, upto and onto the secretory cell held on the selective electrode. This second procedure is referred to here as a "cell transfer operation". In the cell transfer operation it is possible to reverse the roles of the secretory and fusion partner cells.

In the third way of bringing the fusee pair of cells together, pre-selected cells of each requisite type are singly and separately introduced into the fusion chamber, without necessarily the use of electrodes in this introduction.

The cell pair is then subsequently brought into opposition by the application of forces which depend on the gradient of the square of the electric field, as for example in the manner of Example 4 below. This cell pair is then completely or partially immobilised such that it is practicable to effect its fusion while it is not attached to either electrode.

Figure 26:
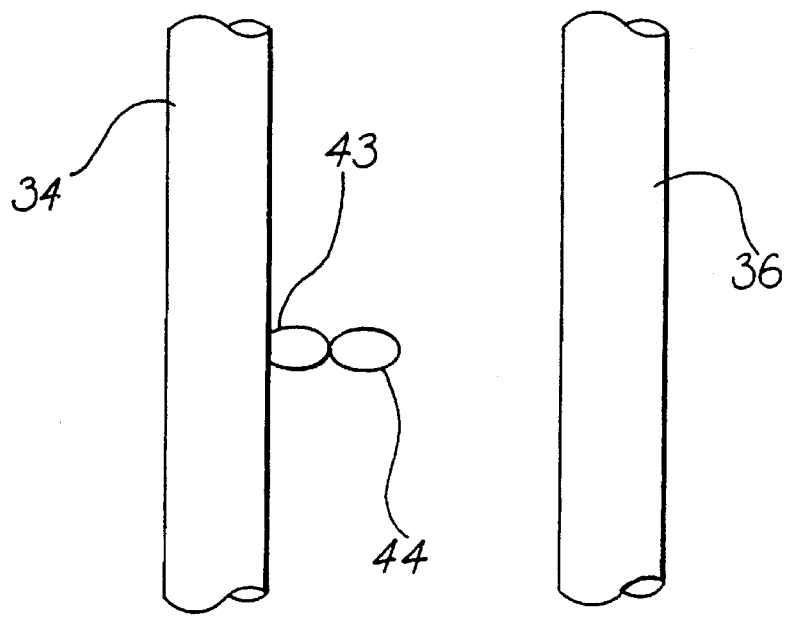
FIG. 26 shows the appression and elongation wrought by the applied fields, prior to delivery of the fusagenic, pulsed electric fields.

While various embodiments are feasible to appose the pair of cells, to achieve suitable fusion it is necessary to employ an AC field of suitable intensity, frequency, waveform, gradient and duration, so as to hold the cells simultaneously under compression and under elongation as illustrated in FIG. 26, and to maintain that contact up to, and including the time of fusing, though not necessarily so, so as to achieve gentle fusion in the manner described in the next section.

4. Fusing the Selected Pairs of Cells

Figure 8:
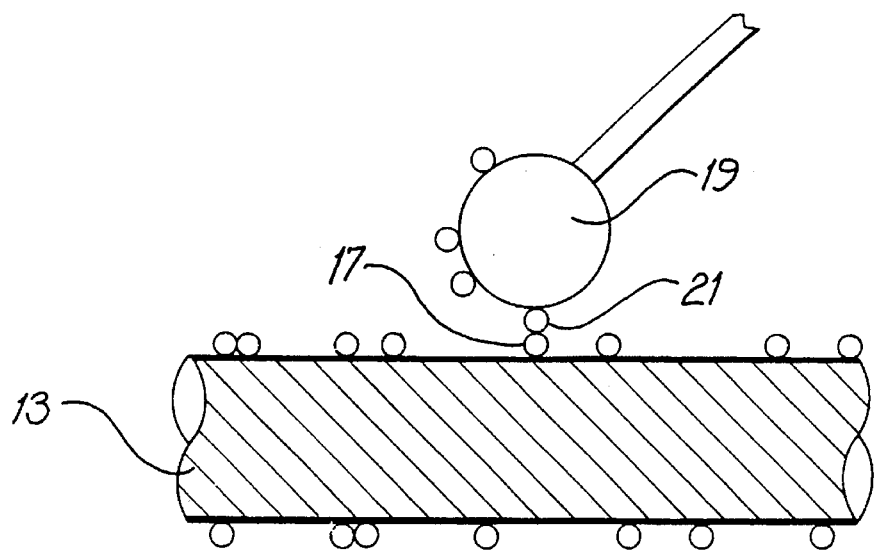
FIG. 8 is a diagrammatic representation of a cell 21 on the electrode 19, of FIG. 7 being brought into close juxtaposition with a cell 17 on the electrode 13 of FIG. 5 to achieve the firm apposition of just two fusee cells, one each of the requisite type.

Once the selected excretory cell and its immortal fusion partner are in firm contact, the cells may be fused by the application of short (microsecond to millisecond) pulsed electric fields (Electrical fusion), the electric pulses being applied between the electrodes bearing the secretory cells and the immortal cells respectively (FIG. 8). In alternative embodiments, the pulse(s) may be applied between the electrode to which the attached partner cell was transferred to rest on top of the selected normal cell using the cell transfer operation (FIG. 20 through 24), and another remote, "fusion" electrode, either with (FIGS. 25 and 26) or without (FIG. 28) either one or both of these electrodes being in contact with the fusee cell pair. Alternatively a fusagenic chemical (for example PEG) or viral mediation (for example Epstein-Barr virus) could now be locally introduced into the chamber, for example via a micropipette (to achieve Chemical fusion), or a combination of electric fields and fusagenic agents (Electrochemical fusion) could be used. After the fusion pulse or pulses are delivered, one may or may not maintain the apposing AC field at its pre-fusion values, though some maintenance of the field has sometimes been found useful to promote the fusion. The simple maintenance of firm appression can be sufficient by itself in some instances to cause the electrical breakdown of the cell membrane which is required for cell fusion, that is without the application of the transient field pulses, and this is treated as an alternative embodiment.

The optimum duration and strength of the electric pulses required depends on the two cell species (including cell sizes), the ionic strength and composition of the aqueous solution, the tonicity of the solution, temperature and other physiological parameters. It is possible, however, to readily achieve over 90% fusion probability for the cell pair, without subsequent lysis of the resultant fusate hybrid cell.

5. Manipulating the Fusates

Figure 9:
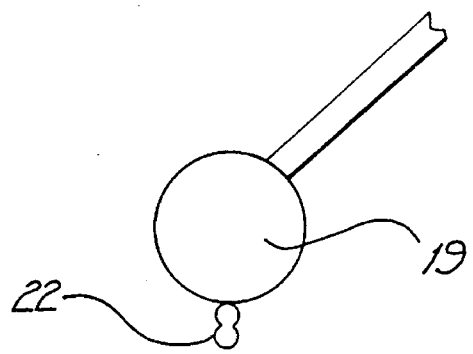
FIG. 9 is a diagrammatic representation of the electrode 19 of FIG. 7 after a binary cell fusion has occurred to produce a fusate cell 22.

There are several standard methods of removing the fusate cell(s) from the fusions described. Cells can be removed using micro-pipettes and/or by manipulating the moveable electrode (attached to the micromanipulator). In the latter case the fusate cell may be held on the electrode by application of a weak alternating electric field between this electrode and a remote indifferent electrode in the solution (FIG. 9). This fusate cell can then be 'deposited' into a 'micro well' built into the fusion chamber, or transported within the aqueous phase to another point for later removal to a culture well.

The "fusates" may also be released from the electrode by exposure to a standard growth medium and/or a solution of enhanced acidity. The "fusates" can then be flushed from the chamber and collected for culturing, or transported by any other suitable means to a culture well.

In a further variation the fused hybrid cells can be left in the fusion chamber, either still attached to, or detached from, the electrode and can be cultured in-situ by replacing the solution in the fusion chamber by a suitable culture medium.

Figure 18:
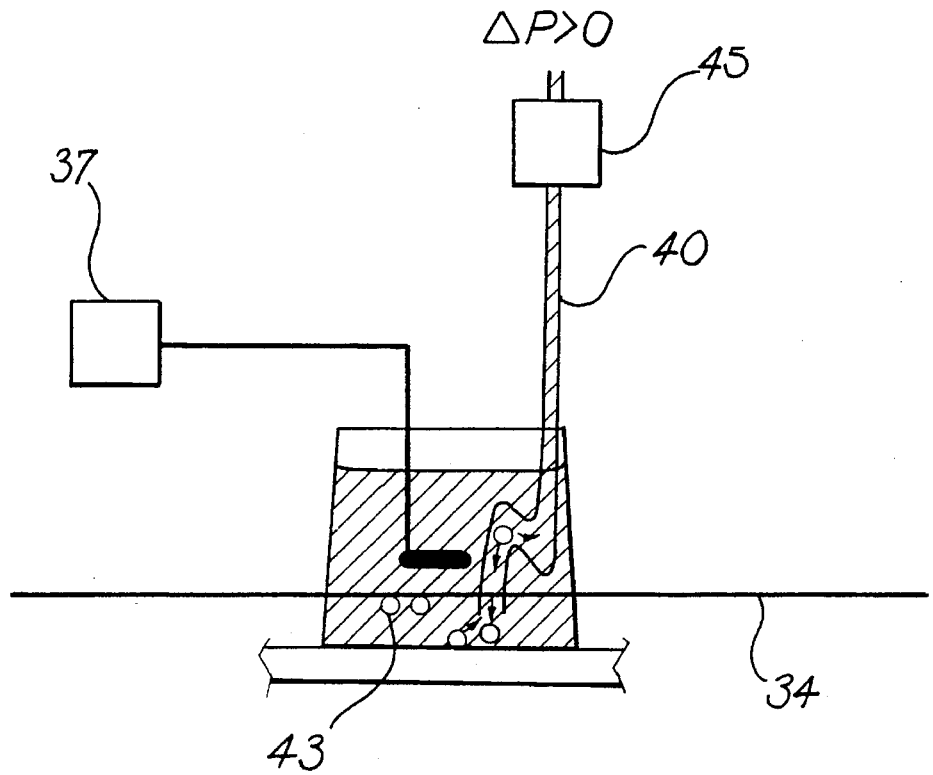
FIG. 18 is a schematic vertical elevation showing the "displacement" pipette introducing fluorescent partner cells into the fusion chamber of FIG. 13.
Figure 19:
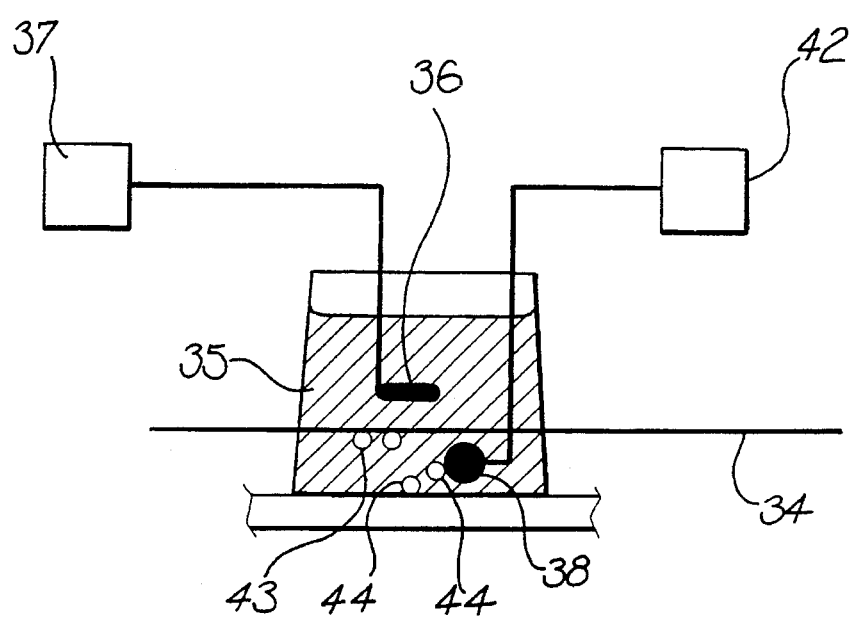
FIG. 19 illustrating the use of the electric fields to pick up partner cells from the cluster of such cells introduced with the displacement pipette as shown in FIG. 18, shown as a schematic vertical elevation.
Figure 27:
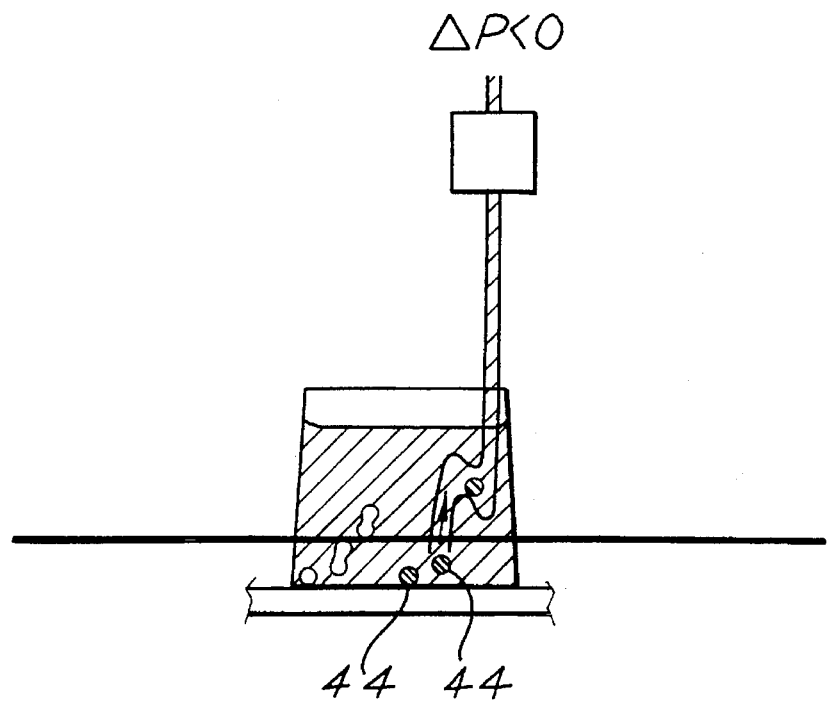
FIG. 27 is a schematic diagram of several cell pairs, post-fusion, attached to the fixed electrode of the fusion chamber of FIG. 13, the displacement pipette is shown withdrawing an unfused partner cell 44.

In an alternative embodiment, the exposure to normal medium may or may not be combined with the deployment of a displacement pipette (for instance as it is shown in FIGS. 18 or 27), of such shape and design that it can be used to withdraw, for example under computer control, a fine volume of the medium, which volume can be simply adjusted by manipulation and/or by computer control, and perhaps with the assistance of the electric fields to effect detachment, so that the fusate cell is also withdrawn into the displacement pipette, far enough for it to pass a U-bend trap or other retaining artifice, see FIG. 27 for instance; thereafter the pipette plus cell may be manipulated out of the chamber through the air, and the cell deposited into a Terasaki- or other culture dish.

6. Short-term outgrowth of the hybrids

Following the fusion, the individual fusate cells are each placed into separate wells containing suitable medium, possibly supplemented with growth factors or feeder cells. After five division cycles, our practice has been to employ limit dilution methods or single cell-dispensing via our displacement pipette, to re-clone the 25 to 30 progeny as single cells into new wells and fresh medium, itself previously cleared of Immunoglobulin G (or Immunoglobulin M,A,E,D, if such secretors are sought in the particular hybridoma), so that we can achieve early detection of the target antibody/isotype production by the subsequent outgrowths in each new well. This allows us to select the useful clones and discard the irrelevant ones, thus minimising the time to finding the stable, successful, clones and reducing the volume of processing.

Wells with high productivity may then be subjected to electrochemical selection by the method described above, to isolate those cells which produce high affinity antibodies (for example see FIGS. 29, 30 and 31), depending on requirements, or expanded as they are, or re-cloned as above, depending on the stability of karyotype (separately measured) and/or as indicated by the antibody production data.

7. Genetic Stability of the Fusates

The genetic stability and associated biomolecule production of the fusates can be verified by the usual techniques of cell culture over extended periods and by employing standard assay techniques for the monoclonal (or other secretory) products, such as, for example, ELISA methods or flow cytometric analysis. Once the cells reach sufficient numbers, karyotyping and also surface Immunoglobulin assay by Flow Cytometry can be performed.

Alternatively, or in addition, the affinity and selectivity of the antibodies produced by the new hybridomas (or other hybrids) can be evaluated and individual hybrids selected using the electrochemical selection technique described above (see FIGS. 29, 30 and 31). In this manner hybrids which show, for instance, very strong affinity for the antigen can be selected from the others and removed separately from the chamber as described. After re-culturing this process could be repeated if required. This re-selection process, of course, does not involve a re-fusion with another partner cell, nor does it involve most of the procedures-required in current routine methods of hybridoma development.

8. Production of Triomas, Quadromas and High Secretors

The selection and fusion process described above can be readily extended to the selection and fusion of two hybridoma cells secreting antibodies to different antigens (quadromas). In this way it will be possible to generate hybridomas which excrete bi-specific antibodies. Fusion of hybridoma cells with secreting B cells ('triomas') would achieve a similar result.

Such antibodies would have widespread applications in diagnosis and therapy, and are already employed in some diagnostic applications.

It is also possible to fuse two identical hybridomas by the technique described. This could be used to produce 'high secretors' of the monoclonal antibody, by repeated fusions of stable binary fusate clones of first hybridomas and then their dihybridoma progeny and so on, thus enclosing multiple copies of the genes within a single hybrid cell. We have already performed such dihybridoma creation programs; see Examples section below.

9. Hybrids of Other Types and Amplification of Existing Constructs

The invention also allows the generation of cell lines by fusing any type of eukaryotes with any defined cell or vector partners, to achieve eukaryote hybrids that can produce natural products in their normal, for example, glycosylated form, particularly but not necessarily secreted molecules, such as interleukins, growth factors, blood products etc.

The invention also allows the fusion of bacterial cells with mammalian cells, to bypass the present production problems found with bacterial vehicles for eukaryotic genes. The rounds of gene amplification described for the hybridomas can be applied to these cells too, to get high secretors, though we do not yet know the limits to the numbers of rounds of gene amplification.

An especially fruitful area of gene amplification is that where mammalian or plant cells (eukaryotes) have been transfected with other genes (often via vectors which integrate their DNA into the chromosomes of their host cells), such as has been done with the human Erythropoietin gene. Sequential rounds of autofusions of these eukaryotic transfect constructs, performed with the unique capabilities of our technique, are likely to yield cell lines which are hyperproductive relative to the present constructs used for routine production of these normally very expensive products.

10. Advantages of the New Method

The new method has, at least in preferred embodiments, the following specific advantages:

i) It requires only very small numbers of cells; tens of cells can be employed to yield numbers of the desired hybrid cells (as against millions required by the current techniques) and may therefore obtain specific secretory cells from for instance peripheral blood of donors. This opens the possibility of producing a very wide variety of human hybridomas and other excretory human hybrid cells, presently unattainable.

ii) Hybridomas of human cells and other species (for instance mouse) may offer advantages such as more rapid culture or more robust hybrids than human— human hybrids.

iii) The new cycle of operations is shorter than the conventional development cycle: it obviates a great deal of the farming and cloning stages; because cells may be grown as clones from the outset, and supernates can be assayed within five days of the fusion, and HAT selection is unnecessary.

iv) It can select the antibodies for highest affinity and specificity, at the time of fusion if so desired; then again start assays very soon after fusion.

v) Since HAT selection is not necessary, the choice of immortal fusion partners has none of the present nutrient sensitivity restraints of current methods.

vi) It can produce new cell lines which are "high secretors" of any particular secreted antibody or other natural product, from successive autofusions of the hybridomas themselves. This permits higher production of antibodies per hybrid cell.

vii) It can make triomas and quadromas, producing monoclonal bi-specific antibodies. Such antibodies will make diagnostic kits and other diagnostic kits based on antibodies cheaper and simpler to make. One specificity can be used to attach the antibody to a substrate or functional agent (fluorochrome, toxin, nuclide, etc.), while the second of the bivalent specificities can be directed to the target "producer" cell, by virtue of its marker expression.

viii) For monoclonal antibodies against human cell surface antigens, for example, a "Human Lymphocyte Antigen", HLA, antigen, the process of selection from human peripheral blood (of persons hyper- immunised to the particular HLA antigen) of secreting cells making antibody to that antigen only and to no other cell surface antigen, is straightforward with this method.

EXAMPLES

We now present a series of examples where we have employed divers embodiments of our methods to make new hybridomas and cell hybrids which themselves produce secreted products illustrative of our capabilities and of potential commercial applications.

Example 1

The mouse hybridoma making antibodies to the keyhole limpet hemocyanin, KLH, antigen A specific example of how the method was used to produce a mouse cell hybridoma secreting antibodies to keyhole limpet hemocyanin (KLH) is described below.

The hemocyanin from the marine mollusc, keyhole limpet, has been used as a model antigen in many immunological studies. It is readily available in a purified form.

The specifics for the field strengths, waveforms and frequencies, chemical composition of the solutions, exposure times and all other parameters here described were found to be effective for the production of this particular hybridoma.

1. Methods

The production of the anti-KLH hybridoma can be broken into five processes.

i) Preparation of mouse spleen cells.

ii) Coating the fixed electrode with KLH protein.

iii) Selection of normal B lymphocytes excreting anti-KLH antibody using the electrochemical/selection technique.

iv) Manipulation of the partner cells, from the mouse myeloma cell line, SP2, to form single fusee pairs.

v) Fusion of the selected pairs of cells.

These processes will now be described in detail.

2. Preparation of the B Lymphocytes

Mature mice (strain Balb/C) were immunised with 400 microliters of a solution containing 0.1 milligram hemocyanin per milliliter of isotonic saline. Immunisation was by injection of the protein into the peritoneal cavity. Ten days after the initial immunisation, the mice were give a "booster" injection of KLH. The immune system of the mice responded to the injection and antibodies were present in the serum of those mice immunised. This was revealed by a standard ELISA test on blood taken from the tails of the immunised mice.

In the ELISA test, the presence of antibodies to the protein was revealed in two steps. First the bases and the walls of small depressions or wells in a plastic plate were coated with the antigen protein. The test solution was then placed in some of the wells. A control solution from an un-immunised mouse was placed in other wells. If the test solution contained antibodies to the antigen, the antibody molecules were then bound to the walls of the well, whereas there was only minor, "non-specific" binding of the control antibodies.

Secondly, the bound antibody was then revealed by exposure to a solution containing enzyme linked sheep polyclonal antibodies directed against mouse immunoglobulin. The enzymes attached to the antibodies converted a colourless substrate to a coloured one. A positive binding event was thus indicated by a colour change.

Spleens were removed from immunised mice and from control mice (that is, mice not immunised) to ensure accurate, controlled results to verify the entire method. The spleens contain a mixture of B and T lymphocytes as well as erythrocytes (red blood cells) and other cell types. Using a standard ammonium chloride lysing technique, 90% of the erythrocytes were removed. The remaining cell suspension contained both B and T lymphocytes. The electrodes selection process was performed on this cell suspension (see Section 3 below).

The spleen cells from the un-immunised (control) mouse were used to verify the efficacy of the selection procedures.

3. The Selection and Fusion Chamber

Figure 10:
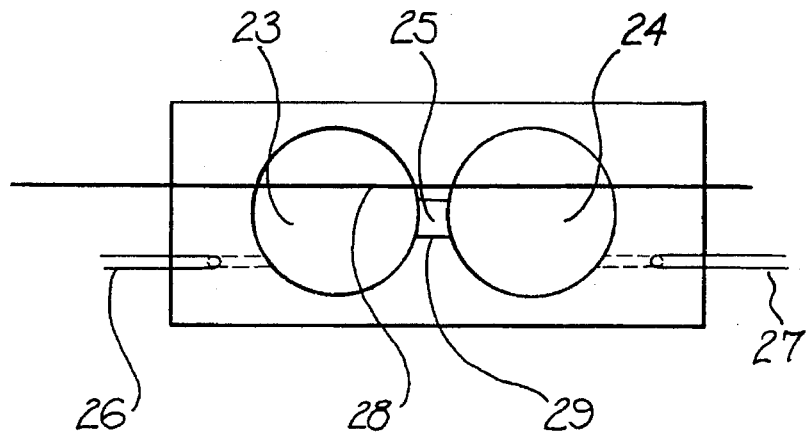
FIG. 10 is a plan view of a reactor cell for carrying out the method according to one embodiment of the present invention.
Figure 11:
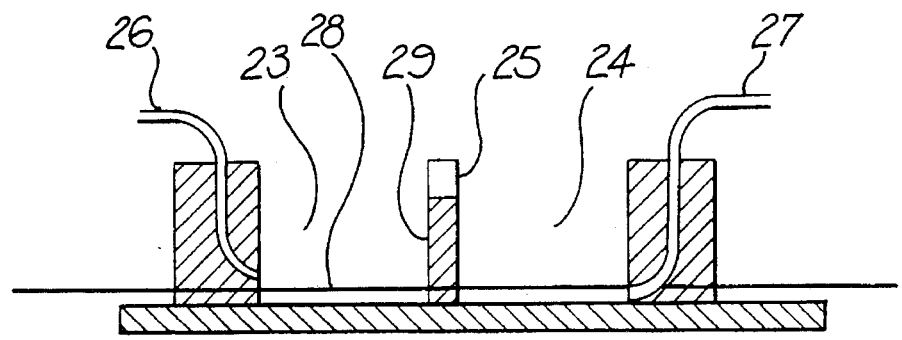
FIG. 11 is a vertical sectional view through the reactor cell of FIG. 10.

A schematic of the chamber used for this particular example is shown in FIGS. 10 & 11. This particular chamber consists of two wells (23 & 24) machined out of a plexi-glass ("Perspex") block. The plexi-glass separating the two wells was also recessed in a channel (25). When the wells were completely filled with solution, the fluid communicated between the wells via this recessed channel. When the wells were filled to 80% of their maximum capacity, the fluid volumes were separated from each other.

The chamber had a flushing system which consisted of two small polystyrene tubes 26 and 27 each two millimeters in diameter; one 26 to allow fluid to be injected (pumped) into the chamber and the other 27 allowed the removal of fluid from the chamber.

A fixed electrode 28 was mounted parallel to the base of the chamber. It ran through both wells and the wall 29 separating them. The wire used was made of a nickel alloy wire and had a diameter of 128 micrometers. It was mounted approximately 0.30 millimeter from the bottom of the wells.

Figure 12:
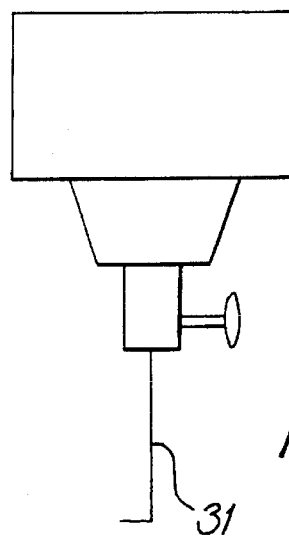
FIG. 12 is a schematic side elevation of a further electrode 31 for use in the reactor cell of FIG. 10.

A second electrode 31 consisted of a small length of the same nickel alloy wire bent into an "L" shape (FIG. 12). This electrode was attached to a hydraulically driven micromanipulator so that it could be moved and positioned at any location in either of the two wells in the chamber.

A third electrode 19 (FIG. 7) was made from a small length of the nickel alloy wire and had an enlarged spheroidal tip, whose radius was approximately 250 micrometers. This third electrode 19 was also attached to a micromanipulator and could be positioned in either of the two wells.

The entire chamber was mounted under a microscope.

4. Preparation of the Cell-Selective Electrode

The fixed nickel alloy wire electrode was coated with KLH protein to make it selective for B lymphocyte cells excreting anti-KLH antibodies.

The steps in this were as follows:

i) The fusion chamber and electrodes were sterilised by repeated washing with 70% alcohol/water solution.

ii) The movable electrode 31 was placed into well 24 using the micromanipulator so that the end portion of the "L" shaped electrode 31 was parallel to the fixed wire electrode 28 and at a separation of one millimeter from it.

iii) KLH protein solution consisting of 0.2 milligram of KLH protein in one milliliter of a sorbitol solution was placed in well 24. The sorbitol solution contained 150 millimolar sorbitol at an acidity of pH=8. The acidity was adjusted by the addition of sodium hydroxide and/or hydrochloric acid.

iv) For this particular example, a DC voltage was applied between the fixed electrode, 28 and the movable electrode 31 (FIG. 10). The fixed electrode 28 was positive with respect to the movable electrode 31. The voltage applied was adjusted so that the electric field in the solution midway between the electrodes was 2,000 volts per meter. The field strength between the electrodes is not uniform, but can readily be calculated using the field equations and the known separations between and diameters of the electrodes. The potential difference was applied long enough to observe (under the microscope) the deposition of a protein coating on the fixed electrode. This required approximately 12 minutes. When the reverse polarities were used, the antigen did not stick to the fixed electrode.

v) The electric potential difference was switched off and the chamber was flushed gently five times with a sterile 150 millimolar sorbitol solution (of acidity pH=8) to remove unbound KLH protein. The flushing was accomplished by injecting more of the sorbitol solution through the small polystyrene tube 26 and removing the solution via the polystyrene tube 27. Finally the chamber was flushed with a sterile washing solution of the 150 millimolar sorbitol, at pH 6.5.

5. Selecting the B Cells

The KLH-coated, fixed electrode 28 was coated with B lymphocytes secreting antibodies to the KLH protein. This was accomplished as follows:

i) The suspension of lymphocyte cells prepared as described in section 2 above was washed twice in a solution containing sorbitol at a concentration of 150 millimolar and an acidity of pH=6.5. Washing was accomplished by spinning the cells in a centrifuge and then resuspending the packed pellet of cells at the bottom of the centrifuge tube in a fresh sorbitol solution.

ii) A sample of the washed lymphocyte suspension in which the concentration of cells was approximately one million cells per milliliter was prepared.

iii) The well in the fusion chamber containing the ligand-coated fixed electrode 28 in well 24 was filled with the suspension of washed lymphocytes.

iv) An alternating, sinusoidal current at a frequency of 2.00 megahertz was passed between the coated electrode and the movable electrode 31, a frequency found to attract the B-cells towards, not repel them from the electrode. The movable electrode 31 was placed in the solution at a depth of about 0.5 mm, parallel to the fixed electrode and laterally separated by about 0.2 mm. At this time the cells in the well were resuspended several times to facilitate their electrochemical/selection with the antigen-coated electrode 28. The level of the current was adjusted so that the alternating electric field midway between the electrodes was approximately 6,000 volts per meter. The electric current was turned on for five minutes and then off for five minutes. The electric field was altered to repel weakly-attached (non-specifically bound) cells from the antigen-coated electrode; this was achieved by switching the frequency of the field to 1 kHz and the amplitude at the point midway between the electrodes was adjusted to 500 volts per meter, values maintained for 30 s. The cycle was repeated. The suspension was then left undisturbed for 10 minutes.

v) At this stage some of the cells from the test mice remained adhered to the coated electrode 28. In the control process, very few cells adhered to the electrode when the lymphocytes were extracted from an unimmunised mouse.

vi) The chamber was then flushed with a solution containing 150 millimolar sorbitol at an acidity of pH=6.5. The flushing was performed at a rate of 3 milliliters per minute. This procedure caused some of the lymphocytes initially adhering to the coated electrode 28 to be removed. The remaining cells were B lymphocytes excreting antibodies to the antigen (KLH protein), for verification step see below. A volume of approximately 5 milliliters of flushing solution was usually enough to remove most of the unattached cells from the well, though their complete removal was not essential, since the cells are normal and usually die without dividing, during the first 2 weeks of cell culture.

vii) In the control experiment with lymphocytes from the unimmunised mice, no cells remained adhered to the coated electrode after the flushing.

6. Verification of the Selection Procedures

The process described here allowed the verification of the selection procedure but was not required for routine production of hybridomas.

The following procedure was used to check that the cells which remained adhered to the coated electrode 28 at the end of the procedure described in section 5 above were indeed B lymphocytes expressing antibodies to the KLH protein:

i) A small quantity of a solution, containing 3 milligrams per milliliter of KLH protein in a 150 millimolar sorbitol solution, pH=7.5, was added to well 24 in the fusion chamber. This was left in place for 30 minutes, at a room temperature of 20° C.

ii) The solution was then washed off gently by flushing with a 150 millimolar sorbitol solution at an acidity of pH=7.5, leaving a solution volume of about 300 microliters (ml)

iii) 30 microliters of a solution of Fluorescein conjugated Goat anti Mouse Immunoglobulin polyclonal antibodies (Silenus-AMD, Hawthorne, Victoria, Australia) were added to the well, gently mixed, then incubated at room temperature for 30 minutes.

iv) The chamber was again flushed gently with a 150 millimolar sorbitol solution at an acidity of pH=7.5 as above.

v) The chamber was illuminated with ultra-violet light and the fluorescence checked under the microscope. Result—More than 95% of the cells adhering to the coated electrode showed fluorescence. That is, more than 95% of those cells were expressing antibodies to KLH protein.

In the control experiment, using unimmunised mice, no cells remained adhered to the coated electrode after flushing (as described in section 5.).

7. Manipulation of Myeloma Cells (SP2)

To effect electrical, binary fusion between the selected B lymphocyte excreting antibody against KLH protein and an SP2 myeloma cell, a single SP2 cell had to be brought into good membrane contact with one single selected B cell which had been isolated using the technique described previously, and left in well 24, as described in step 5 (vi) above.

To do so, a movable enlarged tip, electrode 19, (FIG. 7) made of nickel alloy wire (diameter 128 micrometers), a micromanipulator, and dielectrophoresis were required. A protocol for picking up a single SP2 cell and inducing fusion with the B lymphocyte is as follows:

i) A suspension of SP2 cells in a solution of 150 millimolar sorbitol at pH 6.5 was prepared, and contained approximately 10,000 cells per milliliter.

ii) Well 24 was filled with a solution of containing 150 millimolar sorbitol at pH 6.5, as described in step 5 (vi) above.

iii) Well 23 was emptied and dried.

iv) Two thirds of well 23 was filled with SP2 cell suspension (from step i). The suspension was left undisturbed for 10 minutes to allow all the SP2 cells to settle to the bottom of the well. The well was then filled gently (so as not to disturb the SP2 cells and thus prevent their accidental transfer through the channel 25 into well 24) with 150 millimolar sorbitol solution such that the sorbitol solutions in both wells 23 and 24 were connected via the channel 25 which was now also filled with the sorbitol solution. The SP2 cells were, however, only present in well 23, and except for a few cells, were lying on the bottom of the well.

v) The movable electrode 19 was manipulated into well 23 using the micromanipulator.

vi) This movable electrode 19 and the fixed electrode 28 were connected to a sinusoidal electrical waveform generator. The electrodes were also connected, in parallel, to an electrical pulse generator. The sinusoidal generator was set to a frequency of 1.8 megahertz and an amplitude of 3 volt, which provided a field intensity midway between the electrodes of approximately 6,400 volts/m, which was attractive for the SP2 cells. This was adequate to produce the preferential movement towards and attachment of SP2 cells to the spheroidal tip of the movable electrode 19 (FIG. 7), by dielectrophoresis in the non-uniform electric field near the electrode's tip. In this case the attachment was not chemical binding as used above in the selection of the secretory cells but was partly electrical selection. In this case any adhesion occurring here was weak and chemically non-specific, such that once the field was suitably altered, the cells would drop off the electrode or could be easily removed by gentle agitation (with the field turned off), or be propelled away from the electrodes (with the frequency shifted to 1 kilohertz).

vii) After one or a few SP2 cells had been attached to the movable electrode 19 that electrode was moved gently into well 24 through the channel 23 making sure that at all times the electrode remained submerged in the sorbitol solution filling the channel connecting wells 23 and 24. The movement of the electrode was effected by the hydraulic micromanipulator to which the electrode was attached.

viii) The SP2 cell attached to the tip of the electrode was next manipulated so that it was facing towards and approximately 5 micrometers distant from one of the selected B lymphocyte cells which were attached to the fixed electrode in well 24.

8. Fusion of Selected Cells

To effect electrical fusion of the selected normal, secretory, B lymphocyte and the fusee, partner, SP2 cell, now paired, the following procedure was used:

i) The electric field between the movable electrode 19 and the fixed, selective, electrode 28 was increased to a value of 50,000 volts per meter. This caused both cells to be at once elongated and firmly attached to the electrodes. The elongation brought the cells into tight contact. This was done to ensure good cell membrane contact. The frequency of the electric field was kept at 1.8 mega hertz.

ii) A few square electric pulses were now applied to the electrodes at a rate of 2 pulses per second, each pulse was 100 microseconds in duration. The pulse amplitude was set to between 3 and 4 volts when the electrode separation was 50 micrometers (suitable for the types of cells in this single fusee pair), field strength circa 65,000 to 70,000 volts/meter. At this stage the single pair of cells fused to form a single fusate cell, though the shape remained indicative of its being a fused pair rather than one normal single cell.

iii) Immediately after fusion the high frequency AC electric field was turned off. The fusate cell remained bound to the fixed electrodes 28.

iv) The movable electrode 19 was moved back into well 23 using the micro manipulator and steps 7 to 8 as described in this section were repeated to effect further binary fusions.

v) After obtaining a few fusates, the fusion medium was removed and replaced with culture medium using the flushing system (tubes 26 and 27) built into the fusion chamber.

vi) The chamber with the "fusates" in well 24 were then transferred into a $CO_2$ regulated incubator for a few days.

At that stage the chamber contained enough cells to allow the cells to be removed from the fusion chamber and plated into the small wells of a standard 96 well incubation vessel. Division of binary fusate cells occurred mostly within 48 hours, in over 90% of cases. Thereafter the cells were treated according to the procedures described in the text of the section above.

In summary, stable, clonal hybrids were isolated and grown in culture following a period of approximately three weeks after the original fusion of the cells.

Example 2

A human-human hybridoma to Hepatitis B surface antigen
1. Methods

The production of the human-human hybridoma to Hepatitis B surface antigen can be broken into five processes.

i) Preparation and pre-enrichment of the human peripheral blood cells.

ii) Coating the fixed electrode with Hepatitis B surface antigen to make it chemically selective.

iii) Selection of B lymphocytes expressing anti- Hepatitis B surface antigen antibody, by electrochemical selection using principally the fixed, selective electrode.

iv) Manipulation of the human partner cells, K562, using electroselection on the transfer electrode.

v) Fusion of the selected pairs of cells, repeated several times to obtain a representative number of hybrid fusates.

These processes will now be described in detail.

2. Preparation and pre-enrichment of the human peripheral blood cells.

Samples of human peripheral blood, 10 milliliters, were drawn from subjects previously shown to be negative (controls) and positive (tests) for the production of Immunoglobulin G antibodies to the Hep B surface antigen. Samples were taken from positive subjects recently boosted with the recombinant vaccine supplied commercially by Smith Kline Beecham, Dandenong, Victoria, Australia. Each sample was processed so as to remove nearly all the cells not of the B-cell lineage, and then to enrich the remainder for the terminal stage secretory B-cells, the plasmablasts and plasma cells. Thus, in each sample, the whole blood was separated over Percoll (Pharmacia Limited, West Melbourne, Victoria, Australia), then depleted of monocytes by plastic adhesion. The resultant cells were panned with OKT3 antibody (pan-T-cell antibody, from Ortho Diagnostics, Ryde, NSW, Australia) then B1 (pan-B-cell antibody, from Coulter Corporation, Brookvale, NSW, Australia) and then NKH1 (a marker for null, for example, Natural Killer, cells; also from Coulter), twice at each stage. Finally the unattached cells from the last of the previous panning steps were panned using the Cluster of Designation 38, "CD38", antibody, obtained from the supernatants of the hybridoma cell line, CRL 8022, (U.S. Pat. No 4,364,935; the cell line was acquired from the American Type Culture Collection, Rockville, Md., USA) and typical of plasma cells, but present also on activated T-cells and an immature B-cell subset. Following several washes with normal saline solution to remove the unwanted cells, that is those not attached to the dish, the attached cells were recovered from the dish, by first detaching them by incubation (30 minutes at 370 C.) with an excess of the CD38 antibody, 10 microliters in 1 milliliter of the subject's own serum, then collecting the loose cells. Cells from several washings were pooled, concentrated and washed; they were resuspended in normal medium plus 10% Foetal Calf Serum, FCS; about 40,000 cells were recovered. These cells, thus enriched for blasts, were subjected to the electrochemical selection procedure using an electrode system, described in FIGS. 13, 14 and 15, which selected for cells which expressed the antibody to the Hepatitis B surface antigen on their surfaces. This is described in Section 5 below.

3. The Selection and Fusion Chamber

Figure 13:
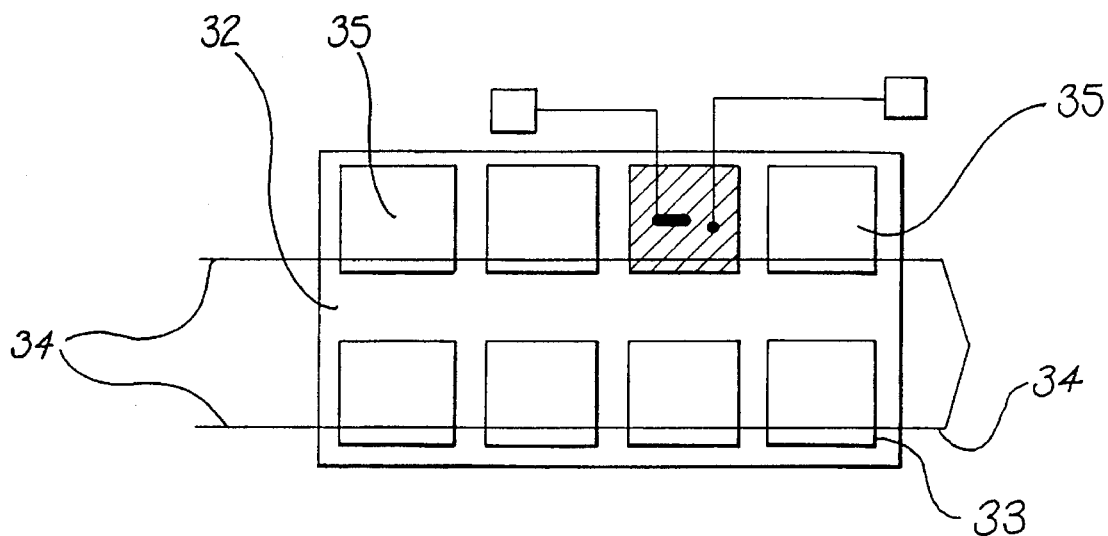
FIG. 13 is a schematic plan view of an alternate fusion chamber for carrying out the methods according to the present invention.
Figure 14:
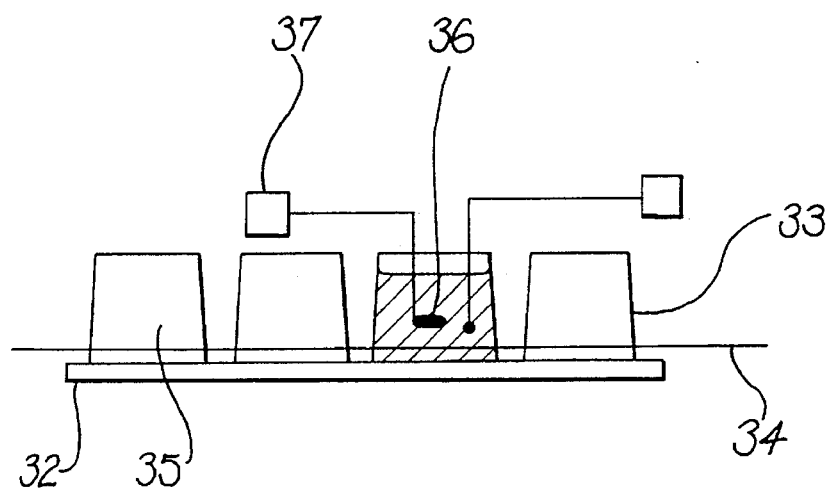
FIG. 14 is a vertical elevation of the schematic plan view in FIG. 13.
Figure 15:
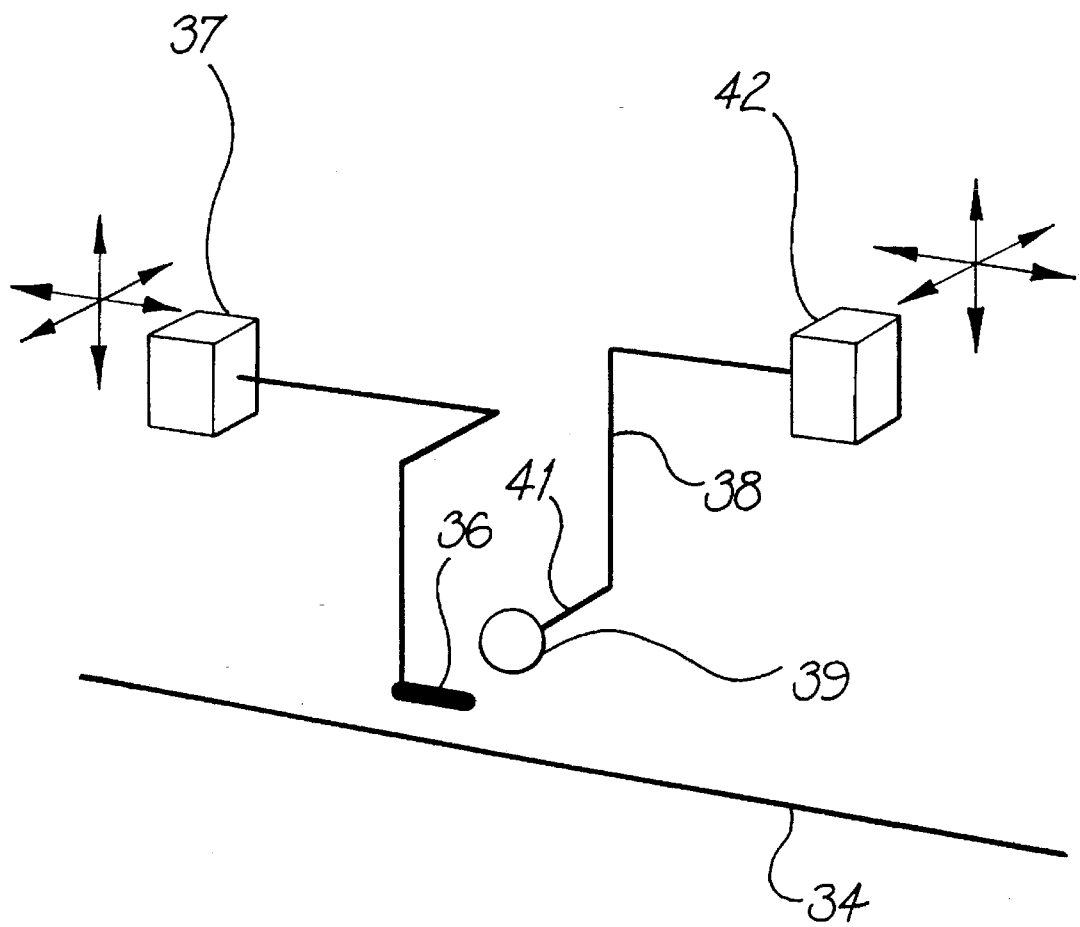
FIG. 15 is an isometric schematic view of the three-dimensional arrangement of the fixed, fusion and transfer electrodes.
Figure 16:
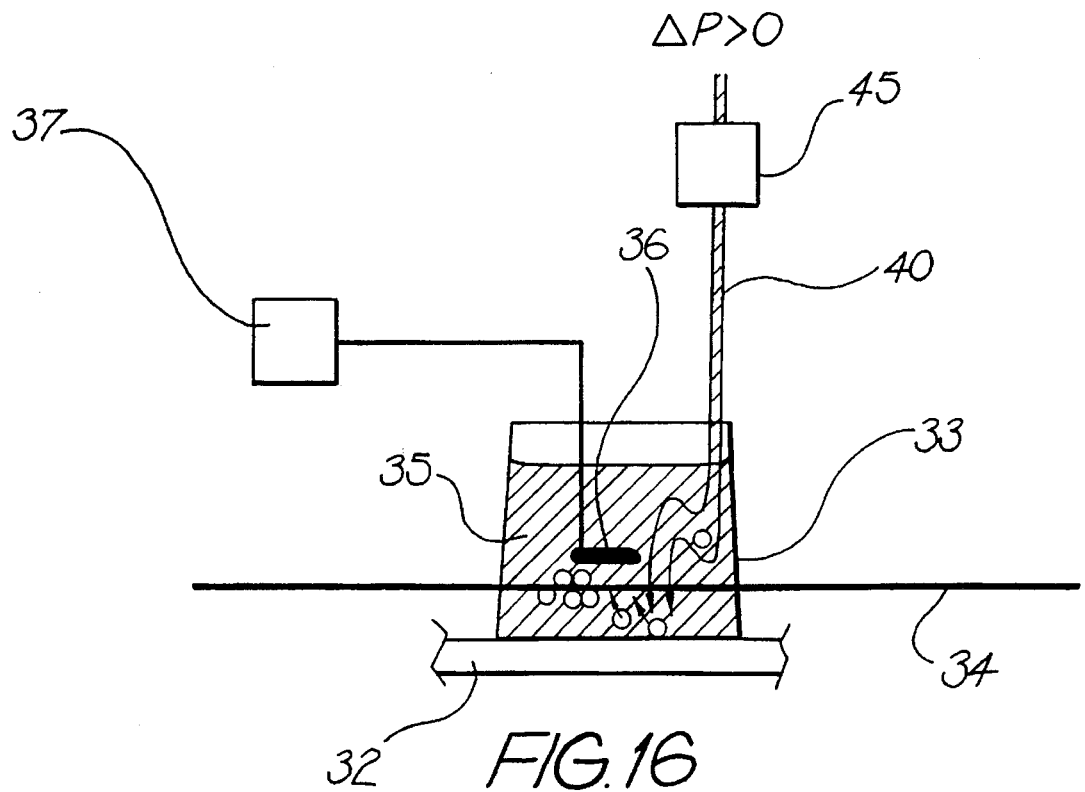
FIG. 16 is a schematic vertical elevation showing a "displacement" pipette introducing secretory cells by the application of positive pressure into the fusion chamber of FIG. 13.
Figure 17:
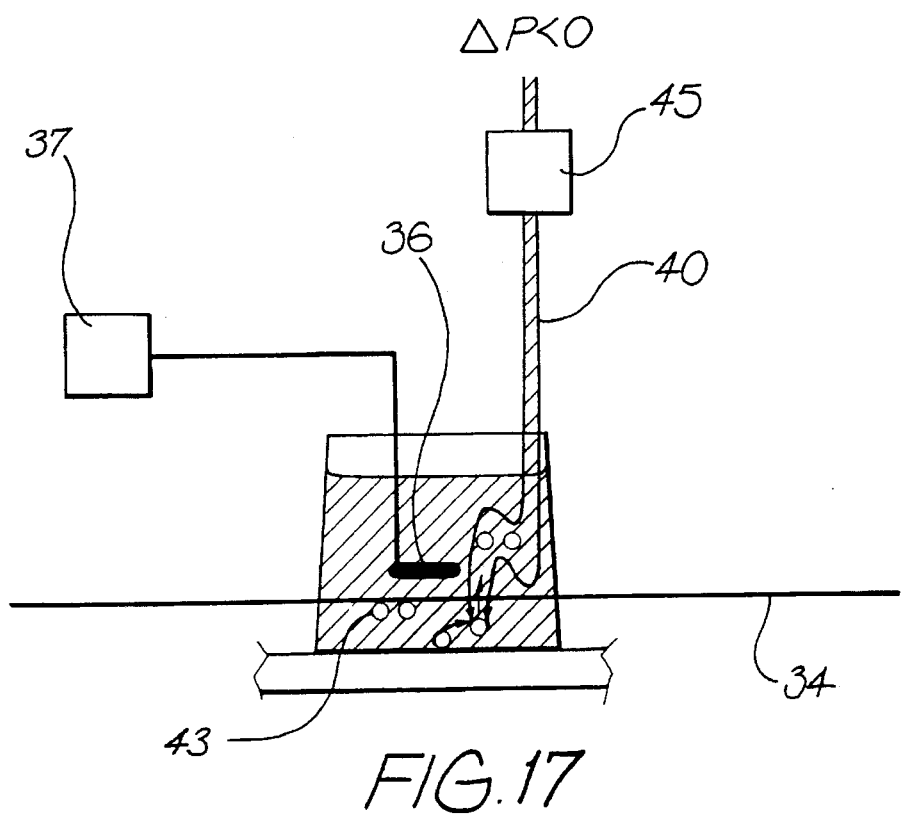
FIG. 17 is a schematic vertical elevation showing the "displacement" pipette withdrawing unattached cells from the fusion chamber of FIG. 13.

The procedures of cell selection and of cell fusion were performed in single wells 35 of "Nunc", eight-well plates 32, purchased from Medos Ltd, Sydney, Australia, and modified for the present purposes. The modifications and the mode of employing the wells and electrodes are shown in FIGS. 13, 14 and 15. Briefly, the plastic strips of wall 33 were lifted off the plate 32 and a single fixed electrode 34 made of alloy nickel wire, diameter 128 micrometers, was laid near to and along the bottom of the wells 35 traversing, via narrow slits cut into the walls 33 of the wells 35, first one set of 4 wells then returning along the bottom of the other 4 wells, the walls 33 were replaced and re-sealed with Silicone rubber adhesive which also sealed the slits through which the wire electrode 34 traverses the wells 35; in any one well 35, the fixed electrode was typically about 500 micrometers above the glass slide bottom 32. The plate 32 was mounted on an inverted microscope (not shown), and attached at one end to a one-dimensional coarse manipulator (not shown), so the the wells could be moved one by one across the stage into alignment with the microscope's optics. A triple pipette, "tri-pipette" (not shown), of fine dimensions suitable for its placement above and manipulation into the chamber to be used, was mounted on a triple axis micromanipulator; in this way the tri-pipette could be brought into position at the optimal position in the fusion/selection chamber for performing its functions of injecting and withdrawing solutions for suspending and washing cells, for washing and flushing the wells 35, and for changing solutions used in the wells. A single pipette 40 (see FIG. 16), the "displacement" pipette, was separately mounted on another triple axis micromanipulator 45; this Was used to transport small numbers of cells to, from and between the wells 35, and was set up so that, under the preferred conditions of cell concentration and pressure control, one could easily withdraw or add to a well, a volume that contained a desired, small, number of cells, be it one, two or five cells.

4. Preparation of the Cell-Selective Electrode Hepatitis B surface antigen was obtained from Abbott Australia Pty Ltd(Kurnell, NSW, Australia) and used for coating the electrode. It was used as a 1 in 10 dilution in 150 millimolar sorbitol at an acidity adjusted using sodium hydroxide and/or hydrochloric acid solutions, of pH=8.0. The fixed nickel alloy wire electrode 34, 128 micrometers in diameter, was coated with the Hepatitis B surface antigen to make it selective for B lymphocyte cells excreting anti-Hepatitis B surface antigen antibodies.

The steps in this were as follows:

i) The fusion chamber, that is, well 35 and electrodes were sterilised by employing the tri-pipette in repeated washings of the chamber and contents with 70% alcohol/water solution.

ii) a fusion electrode 36 was placed into the active well 35 (that is the well in which the present activities were performed, as a preparation of the well for use in fusing one cell pair in that well) using its dedicated micromanipulator 37, so that the proximal end of the electrode 36 was parallel to the fixed, selective, electrode 34 and at a separation of one millimeter from it, and the well flushed 5 times with the 150 millimolar sorbitol, pH 8.0, circa 1 ml each time, before draining it completely, prior to adding the antigen solution.

iii) 0.5 ml of the antigen solution was placed in the active well 35 ready to make the fixed electrode chemically selective.

iv) For this particular example, both a DC and an AC voltage was applied between the fixed electrode 34 and the movable, fusion electrode 36. The polarity of the DC potential applied was such that the fixed electrode 34 was positive with respect to the fusion electrode 36. The voltage applied was adjusted so that the electric field in the solution midway between the electrodes was 4,000 volts per meter. The applied AC potential had a frequency of 1.7 Megahertz and the average AC field strength of 2,000 volts/meter. The electric field midway between the electrodes can be calculated from the applied potential, the electrode separation and the diameters of the electrodes. The potential difference was applied long enough to observe (under the microscope) the deposition of the chemical coating on the fixed electrode 34, about 10 minutes in this case, at which time the field was reversed in polarity for a further 2 minutes. Similar coatings were generated on different fixed, selective electrodes 34 in other wells 35 where the polarity of the DC field was reversed for one and ten minutes respectively. These were successfully employed in cell selections and then pairwise fusions in some other hybrid fusions.

v) The electric potential difference was switched off and the tri-pipette used to gently flush the chamber five times with the sorbitol solution to remove unbound Hepatitis B surface antigen. The chamber was then evacuated and a new solution added, of 150 millimolar sorbitol now of pH=6.5, ready to receive the secretory cells for electrochemical selection.

5. Selecting the B Cells

The electrode 34 was coated with cells enriched for B-cell blastoid cells 43, secreting antibodies to the Hepatitis B surface antigen.

This was accomplished as follows:

i) The suspension of lymphocyte cells prepared as described in section 2. above was washed twice in a solution containing sorbitol at a concentration of 150 millimolar and an acidity of pH=6.5, then resuspended at a cell concentration of approximately 1,000,000 per ml.

ii) An aliquot of 50 microliters of the secretory cells 43 was added to the active well 35 containing the fixed, and now chemically selective, electrode 34.

iii) An alternating, sinusoidal current was switched on 30 seconds before the cells 43 were injected; it had a frequency of two megahertz, and was passed between the fixed, selective, electrode 34 and the fusion electrode 36. The level of the current was adjusted so that the electric field at the surface of the fixed, selective, electrode 34 was approximately 8,000 volts per meter, as calculated from the geometry of the electrodes and the applied potential. The electric current was turned on for two minutes and then altered to repel weakly-attached (non-specifically bound) cells from the fixed, selective, electrode 34; this was done by switching the frequency of the field to 1 kHz and the amplitude to 1,000 volts per meter, values maintained for 5 s. The cycle of 2 minutes of attraction mode, followed by 5 s of repulsion mode was repeated four times more. The suspension was then left undisturbed for 10 minutes.

v) At this stage some of the cells 43 remained adhered to the coated electrode, and the unattached cells were recovered for re-use, by gently flushing out the unattached and only loosely attached cells, while replacing the solution with a similar sorbitol solution to that used in the current selection. The removal of loosely adherent cells was assisted by the application of the repulsive electroselective force (1000 volts/meter electric field strength at the surface of the electrodes and 1,000 Hertz). The cells 43 were washed twice with approximately one ml of the sorbitol solution, then the chamber was readied for receipt and selection of the partner, K562 cells 44. The cells 43 which remained attached to the fixed, selective, electrode 34 were presumed to be excreting antibodies to the antigen.

6. Manipulation of Partner Cells (K562)

To effect electrical, binary fusion between the selected lymphocyte cell 43 excreting antibody against Hepatitis B surface antigen and a K562 partner cell 44, a single K562 cell 44 had to be brought into good membrane contact with one of the selected antibody secreting lymphocyte cells 43 which had been isolated using the technique described previously. For this purpose, a "transfer" electrode 38 was constructed which consisted of a sphere 39, 250 micrometers in diameter, attached to a cylindrical shaft 41, diameter 128 micrometers. The electrode was made from nickel alloy wire manufactured by the California Fine Wire Company, California, USA.

Figure 20:
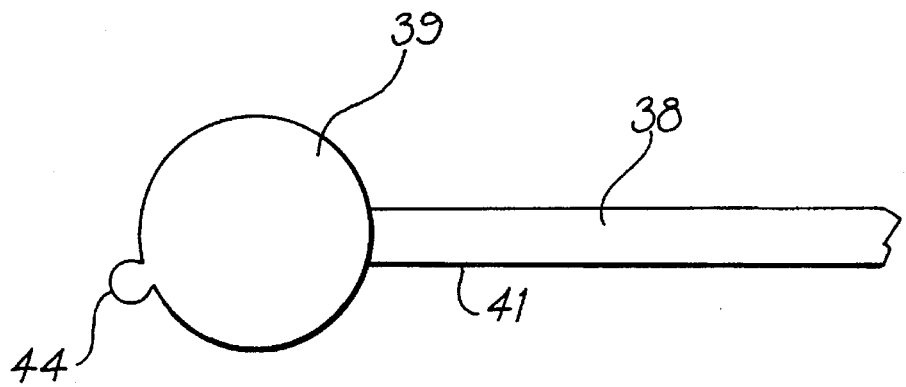
FIGS. 20 to 24 are a series of enlarged schematic diagrams in plan view illustrating the cell transfer operation, the process whereby a single partner cell is attached to a normal secretory cell to form one fusee cell pair in the configuration preferred for cell fusion.
Figure 21:
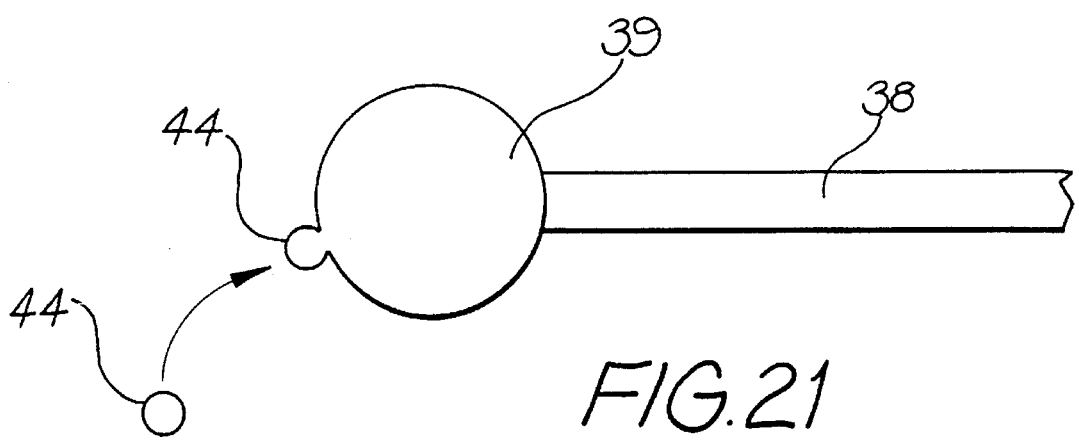
Figure 22:
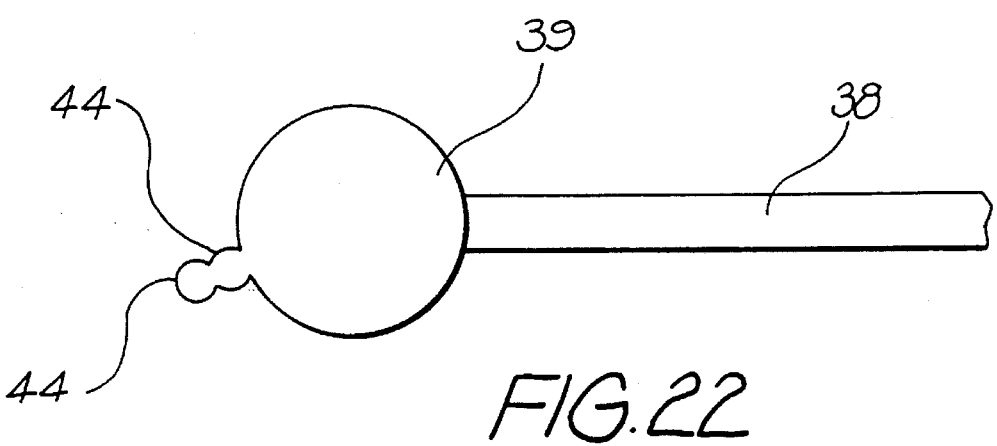
Figure 23:
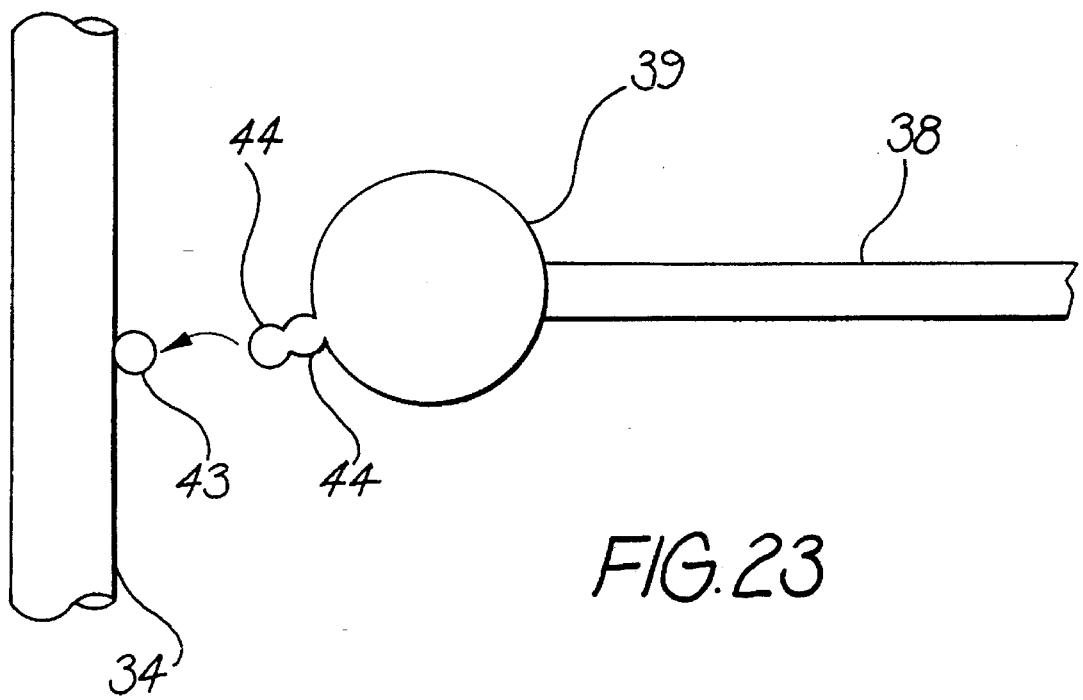
Figure 24:
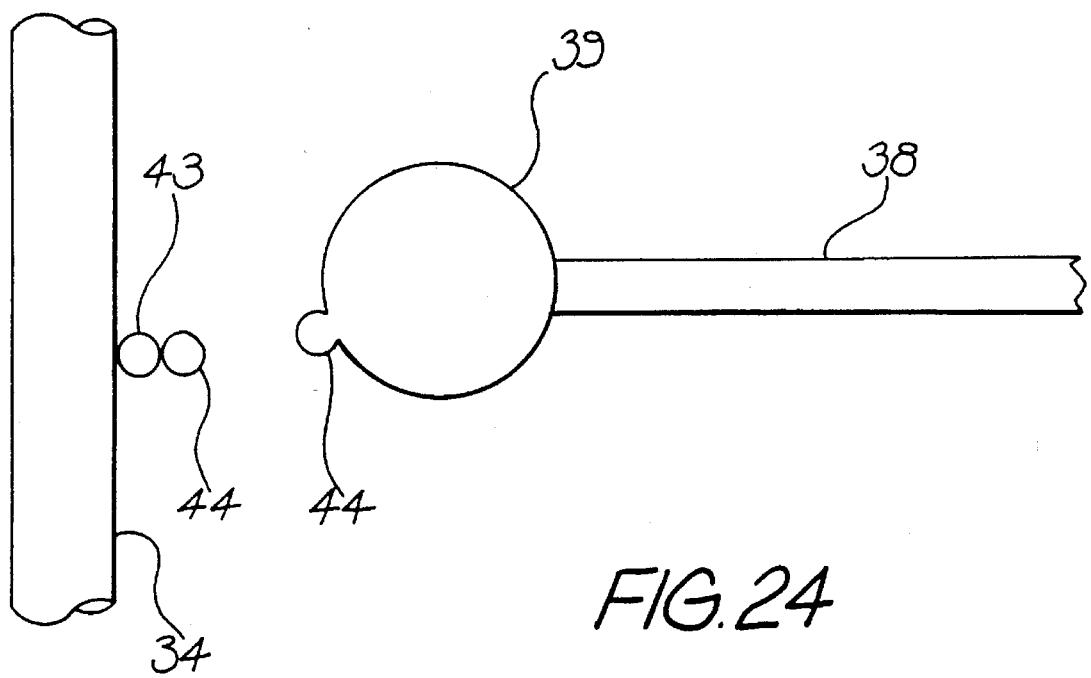

The transfer electrode was mounted in a triple axis micromanipulator 42. A cell transfer operation, was employed here and involved the following steps:

i) A suspension of K562 cells 44 in a solution containing 100 millimolar sorbitol was prepared, and contained approximately 10,000 cells per milliliter.

ii) The transfer electrode 38 was manipulated into active well 35 using its micromanipulator 42.

iii) The fixed electrode 34 and the transfer electrode 38 were connected to a sinusoidal electrical waveform generator. The fixed, selective, electrode 34 and the cylindrical (wire) fusion electrode 36 were also connected, to an electrical pulse generator. The sinusoidal generator was set to a frequency of 2 megahertz and an amplitude of 1 volt. This was adequate to produce the movement and attachment of K562 cells 44 to the tip of the transfer electrode 38 (by dielectrophoresis in the non-uniform electric field near the tip of the transfer electrode). At that stage the situation was like that illustrated in FIG. 20. The electrode was then maneuvered within 500 micrometers of another K562 cell 44 and by a combination of mechanical movements of the electrode 38 and the adjustment of the strength of the electric field, the second K562 cell 44 was attracted to and caused to be held on the top of the first K562 cell, already held onto the transfer electrode; this sequence is shown in FIGS. 20 through 22.

iv) After the second K562 cell had been attached to the transfer electrode 38 the electrode with the "partner" cell attached was moved gently to a position where the second K562 cell, still held on top of the first K562 cell on the transfer electrode 38 was next manipulated to a position approximately 100 micrometers from a normal secretory, lymphocyte, cell attached to the fixed, selective, electrode 34. The movement of the electrode was facilitated by the hydraulic micromanipulator 42 to which the electrode 38 was attached. The transfer electrode 38 was then moved further towards the secretory lymphocyte and then away from it, at a rate of approximately 20 micrometers per second, whilst the AC signal was changed sequentially as follows: the frequency was reduced to 1,000 Hertz, with a potential of 0.5 volts being applied; this caused the second, outermost, K562 cell 44 to detach from the first K562 cell 44 on the transfer electrode 38; the frequency was then altered to a value of 450 kilohertz and the amplitude to 3 volts as the transfer electrode 38 plus first K562 cell 44 were being moved away from the selective electrode 34. During this motion the freed K562 cell 44 moved rapidly under the action of the field, moving towards and becoming held onto the previously chosen, normal secretory cell 43 already on the fixed, selective, electrode 34 as shown in FIGS. 23 and 24 in plan view.

7. Fusion of Selected Cells

Figure 25:
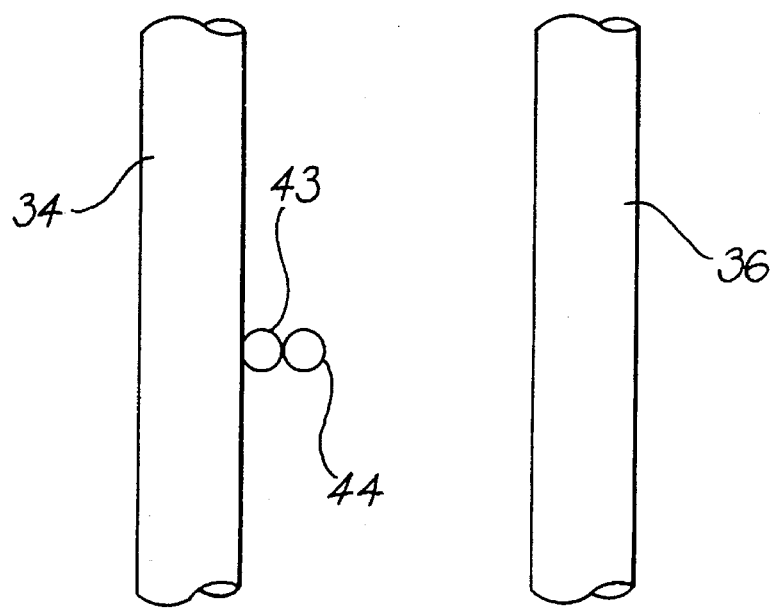
FIG. 25 is a schematic diagram of one cell pair ready for fusion.

To effect electrical fusion of the selected lymphocyte cell 43 and the K562 cell 44, the following procedure was used:

i) The spheroidal transfer electrode 38 was maneuvered gently away from the fixed electrode 34, and the fusion electrode 36 was moved close and parallel to the fixed electrode 34 which had the fusee cell pair attached. The situation was then as shown in FIG. 25 in plan view.

ii) The electric field between the fusion electrode 36 and the fixed electrode 34 was increased to a value of 50,000 volts per meter. This caused both cells to be rapidly elongated with the secretory cell held firmly to the fixed electrode 34. The elongation brought the cells 43 and 44 into tight contact. This was done to ensure good cell membrane contact. The frequency of the electric field was kept at 2 megahertz.

iii) A few square electric pulses were now applied to the electrodes 34 and 36 at intervals of 2 seconds, each pulse being 100 microseconds in duration. The pulse amplitude was set to between 8 and 9 volts when the electrode separation was 50 micrometers (suitable for these two cell types). Usually one or two pulses were enough to cause fusion.

iv) Immediately after fusion the high frequency AC electric field was turned off. The fused pair of cells ("fusate") remained bound to the fixed electrode 34.

v) The transfer electrode 38 was moved back into position after the fusion electrode 36 was moved some distance away, using the micro manipulator 37 and steps 6 through 7 as described in this section were repeated to effect further binary fusions; in many cases, we found it desirable, to complete only one fusion sequence in a given well 35 so that only one fusate cell was then present in that well 35.

vi) After obtaining one or a few fusates, the fusion medium was removed and replaced with culture medium using the tri-pipette flushing system to the fusion chamber; a new well was brought into view and the whole process repeated until there were fusate cells in all the wells.

vi) The whole 8 well plate with the fusion chambers and the fusate cells was then transferred into a $CO_2$ regulated incubator for a few days. At that stage the chamber contained enough cells to allow the cells to be removed from the fusion chamber and plated into the small wells of a standard 96 well incubation vessel. They were incubated in these wells for two days and the cells from the individual wells were then cultured subsequently in larger culture vessels.

Example 3

The mouse-mouse-dihybridoma to be MUD50 antigen

Pairs of clonal cells from the mouse-mouse hybridoma, MUD50, were fused with each other to produce binary fusate cells, which were then placed into culture. Following a round of outgrowth and cloning, we obtained 7 clonal dihybridoma cell lines which appeared to be of stable karyotype and which secreted the original monoclonal antibody. Preliminary screening of these lines, by flow cytometry, disclosed several progeny cell lines which secreted antibody at a greater rate than the parent hybridoma cell line. One such daughter cell line, MUD50B, was characterised for productivity by quantitative enzyme-linked immunosorbent assay, ELISA, as having cells with an average secretion rate per cell (of the whole antibody) which was 70% higher than the average secretion rate per cell of the parent cell line.

Most of the pertinent steps used in this procedure have been detailed in the previous two examples of our methodology. The following description is therefore quite discursive.

1. Methods

There were four main stages in the generation of the dihybridomas:

i) the production of binary fusate cells and their placement into culture, ii) screening of the outgrowth wells for enhanced producers of the antibody, iii) expanding the enhanced producer clones, iv) screening for continued high production of whole antibody of proper specificity.

2. The Cells and their Preparation for Pairwise fusion

The original hybridoma, MUD50, was a gift from Professor KL Williams of Macquarie University, NSW, Australia. MUD50 was made from the PEG-induced fusion of spleen cells of Balb/C mice immunised with a membrane preparation of cells from the slime mould, *Dictyostelium discoideum*, with cells from the HAT-sensitive mouse myeloma cell line, NS1. The hybridoma secretes antibodies of an immunoglobulin $G_3$ isotype, directed against one epitope of a membrane protein expressed in the head region of those cells of the organism which appear during the multicellular, but not the single cellular, phase of the slime mould's growth.

The cells were karyotyped by image analysis of metaphase spreads, courtesy of Dr Lam Poh Tang, Prince of Wales Hospital, Randwick, NSW, and the antibody production rate, measured as the concentration of antibody in the culture supernatant at two different cell concentrations and as the average relative intensity, measured by flow cytometry, of the binding of a fluorescent, goat anti-mouse polyclonal antibody attached to these cells (the same cultures) and to NS1 cells as a control.

Cells grown to a maximum concentration of 1 million per ml were split three to one the day before the fusions were done. Cells were readied for fusion by harvesting approximately 100,000 cells in their log phase of growth, concentrating them by centrifugation, then transferring them into new medium to achieve a concentration of circa 1 million cells per ml. 10 microliters of these cells were then placed into 500 microliters of normal medium, RPMI 1640 (Cytosystems, Melbourne, Victoria, Australia) plus 10% FCS, which had been previously added to one well of a Nunc, 8-well plate, this well was then used as a "holding" well for transfers of small numbers of cells to the remaining wells, as required and just in time for pairwise fusion (Refer to FIGS. 13, 14 and 15; also see Example 2, Section 3). A second well was filled with one ml of 150 millimolar sorbitol solution, made without any adjustment to its pH, so as to minimise its conductivity. This was used as a "washing" bath for the MUD50 cells at the start of each fusion cycle, when circa 100 cells were withdrawn via the displacement pipette (for a description, refer to the end of Section 3 of the Example 2, above) from the holding well and placed into the sorbitol-containing washing well; with the aid of the microscope, the displacement pipette was used to transfer five cells from the washing well into the first of the remaining six wells where single binary fusions were to be performed. After each fusion well was used for a successful fusion, the washing well was fully evacuated of sorbitol and cells, via the tri-pipette, and a fresh solution of sorbitol added to it, with a preliminary rinse-out after 3 fusions were finished.

3. Binary Cell Fusions

Just one fusion was performed in each of the six remaining wells of the 8-well plate. We did not need to chemically coat any of the three electrodes (refer to FIG. 15) in this case, though the addition of a coating of an indifferent chemical did reduce the mortality-rate, post fusion, of the fusate cells. By pre-loading the partner cells with Carboxy fluorescein diacetate (Sigma Chemicals, Sydney, NSW, Australia—as 1 microgram added in 20 microliters of normal saline to the holding well, 15 minutes before any fusions were started) we were able to employ the fluorescein optics of the fluorescent microscope to visualise and then count a small number of intact MUD50 cells introduced into each fusion chamber by the displacement pipette, prior to fusing two of the cells (refer FIG. 16); this feature later assisted in the removal from the wells of every live cell that had not been fused. To attach just two MUD50 cells to the fixed electrode in any one of the fusion chambers/wells, we would set up a field of approx 20,000 v/m, between the fixed and the remote fusion electrode, introduce five cells into the well together, and employ electroselection at 1.95 megahertz, to attach two of the cells to the fixed electrode, separate from each other and on its inside surface facing the fusion electrode. With the assistance of the transfer electrode (refer to FIGS. 19 to 22), the third cell and fourth cells were picked up and then employed in a transfer operation (see also FIGS. 23 and 24) to deposit the fourth cell onto one of the two cells attached to the fixed electrode, and thus to form a fusee pair of two MUD50 cells. The movable fusion electrode was brought up to the position suitable for fusion (refer to FIG. 25) as described in Example 2, Section 7, and the cells were then simultaneously elongated and firmly appressed, by increasing the field to 50,000 volts/meter at the point midway between the fixed electrode and the fusion electrode. The cells were fused by the application of 100 microsecond DC pulses, of intensity 100,000 v/m; usually one but sometimes up to three pulses were used, depending on the response of the fusee pair to the initial pulse(s), as observed via the microscope during the 30 to 60 s following the application of the preceding pulse. Once fusion had occurred, the second single cell (still on the fixed electrode) was sometimes fused with the remaining, fifth, cell. In any event, the displacement pipette was used to remove any remaining living, single, cells from the fusion chamber (see FIG. 27), sometimes using the green internal fluorescence to find counted cells which may have drifted away from the place where they were deposited, to one side of the well. The tri-pipette was immediately used to simultaneously dilute with normal medium [RPMI 1640+FCS, 10%, with the antibiotics, Penicillin/Streptamycin at 0.1 mg/ml (Cytosystems P/L, Castle Hill, NSW, Australia) ] and withdraw the sorbitol present in the well, until only traces of sorbitol were left in the well.

When all six available wells each contained one or two fusates, the 8 well plate was itself covered and placed into a humidified $CO_2$ incubator. In all, 10 plates were completed and their contents placed in culture. At the same time we set up a plate which contained single original cells of the MUD50 cell line sampled from the same culture as the cells we fused. These cells provided a control sample to compare with the binary fusates, for both the division (growth) rate, of the fusate cells and their antibody production rates.

4. Outgrowth and Screening

The wells were monitored every two days for regrowth, and once the cell numbers in any one well had reached reached circa 1,000 cells, it was screened for antibody production by quantitative ELISA. The supernates of the wells were assayed using a Sheep anti-mouse IgG antibody and read on an automated plate reader. Of the 20 wells which showed clearly higher (by a plate reading of 0.3 units greater than the densest control plate) production rates of antibody than the parent cell line, we selected ten that also had higher growth rates, assayed them for light chain production (Sheep anti mouse, anti-kappa light chain antibody coupled to horse radish peroxidase (from CSL, Parkville, Vic, Australia)), and put the seven positive wells into expanded culture. We made a direct comparison between these cell lines each week of the stability of their antibody production, by flow cytometric measurement of the relative fluorescence intensities of cells of each cell line in the series, dual labelled with Fluorescein-conjugated anti-mouse IgG antibody and with Phycoerythrin-conjugated anti-kappa antibody; this was made easier by maintaining the cell cultures at a concentration of $5\times10^5$ cells/ml by daily adjustment of the medium volume. Over the period of the next month four of the lines maintained constant relative fluorescences, while the others showed a decline in the light chain fluorescence. After a further four weeks of monitoring, the most productive cell line, MUD50B, was chosen for full characterisation and for storage.

5. Comparison of Parent and Offspring Cell lines

The cell line was karyotyped, and found to have a modal chromosome number of 84, 4 chromosomes higher than the parent cell line MUD50. The antibody production rates were then measured, on the two cell lines, using two different culture methods to obtain the average cellular antibody production rate, and measured by an absolute and a relative method, namely by quantitative ELISA and flow cytometry. On both measures the offspring cell line was approximately 70% [85 and 65] greater than the parent cell line.

Example 4

Hybridoma from Fusing just an Electroselected Fusee Pair

An example is given of one way that it is possible to electroselect two cells to achieve the geometric configuration required of two fusee cells, and then to fuse them without either of them being in contact with either electrode at that time, and without necessarily employing electrochemical selection of cells onto one or other of the fusing electrodes.

We detail the descriptions of just the processes of pair formation, and their subsequent appression, elongation and fusion, where the normal secretory cells were human peripheral blood cells, antibody positive for Hepatitis B surface antigen.

1. Cells

The normal human blood cells employed in these fusions were prepared by enriching a sample of human peripheral blood for lymphoblastoid cells, using the OKT10 mouse antibody, after first depleting the cells of unwanted and cross-reactive cells, as described in Example 2, Section 2, and the fusion partner cell line was SP2, taken from a culture of cells in the log phase of their growth.

2. The Fusion chamber

The fusion chamber was one well from an 8 well plate, set up and employed as described in Section 3 of the 2nd Example.

3. Selecting the B cells

About 40,000 blood cells, pre-enriched for blasts as described above, were panned to select the cells with antibody to the Hepatitis B surface antigen expressed on their surface. Linbro EIA 96 well flat bottom plates were used to make the panning surface, by overnight incubation with the antigen as obtained from Abbott Australasia Pty Ltd, Kurnell, NSW, Australia, in saline solution buffered to pH 9, and then blocked with bovine serum albumin, 1 mg/ml in normal saline. Selection was made in two of the prepared wells, to which circa 20,000 cells each were added, incubated for one hour at 37° C., then gently washed twice with medium, before the application of 50 microliters of the original antigen solution to cover the adhered cells, and promote their release. After 30 minutes, the well was filled with fresh medium, and this too was replaced once the cells had fallen to the bottom.

4. Preparing the partner cells

SP2 cells were prepared in the same fashion as the MUD50 cells were previously, see Example 3, Section 2. Briefly, 200 SP2 cells from their log phase of growth were placed into 0.5 ml of normal medium in one well of the Nunc 8 well plate designated the "holding" well for these partner cells. A second well was filled with sorbitol solution (pH 7.5) for washing the cells just prior to fusion. A small number of the SP2 cells was transferred into the washing well 5 minutes before one of them was to be transferred into the fusion chamber, using the displacement pipette.

5. Readying the selected normal cells for pairing and fusion

The circa 200 selected normal cells in each of the two wells of the Linbro plate were resuspended and transferred wholly into a third well of the 8 well plate which already contained the holding well for the 200 odd partner cells and their own washing well. Finally a fourth well was filled with the sorbitol solution, to act as the washing well for the normal cells prior to manipulation and selection.

6. Forming just one pair of selected cells

Figure 28:
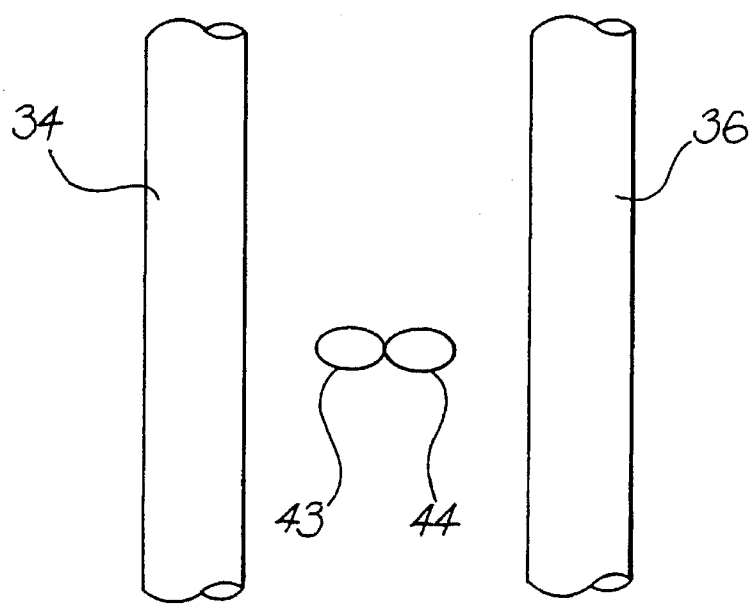
FIG. 28 is a schematic diagram showing a fusee pair of cells, comprising one selected cell of each requisite type, in place in the solution between two electrodes, but not touching either of them, and under the state of appression and elongation wrought by the applied fields, prior to the delivery of the fusagenic pulsed electric fields via the two electrodes.

The displacement pipette was used to pick up just one SP2 cell from the small number placed in the partners' washing well five minutes previously, and then introduce it into the well which had been set up for fusion, and contained a fixed electrode and a movable fusion electrode, there being an AC field applied between the two electrodes, of frequency 2.00 megahertz and intensity, midway between the electrodes of 20,000 volts/m. As the cell fell towards the bottom of the well, it was attracted upto and onto the fixed electrode. The pipette was then used again to pickup and then transport into the fusion chamber, one normal secretory cell from its washing well, where (with a few other cells) it had been placed five minutes previously. Once introduced, the normal cell was drawn gently onto one of the two electrodes by the dielectrophoretic force. When the normal cell fell to the bottom of the well without attaching to an electrode and finished in an area outside the space between and below the two electrodes, the movable fusion electrode was lowered and moved so as to exert an attractive force on the normal cell, moving it onto the fusion electrode. We then moved the fusion electrode back up to a position where it was at about the same depth as the fixed electrode, and now about 300 micrometers away from it, with the two cells more or less in line with each other, placed so that they could be eventually be brought into appression (as shown in FIG. 28). The field intensity was now reduced to circa 500 v/m, and the frequency reduced to 1,000 Hertz, so as to detach the two cells from their respective electrodes and to repel them into the space between them. Once the cells were within five to ten cell diameters of each other, they were brought into apposition by again changing the field frequency to 2.0 megahertz and the intensity to 20,000 v/m. Sometimes the cell pair would then drift toward one of the electrodes, and if left, the pair would then come to rest at one point on that electrode. Where this drift started, we turned off the field, allowed the two cells to fall to the bottom of the well, then lowered the fusion electrode almost onto the well bottom, and turned on the field again. The cells invariably formed a pair, and now stayed put on the bottom of the well, even at mid-point field strengths slightly higher than before, 70,000 to 80,000 v/m. Sometimes the pair did migrate together towards one electrode, but now much more slowly as if impeded by the friction coming from contact with the bottom of the dish, and they could always be fused while not in contact with the electrode(s).

These cells were stretched and apposed (see FIG. 28), then fused by the application of electrical pulses in the same way as we described for the Example 3, Section 3. Subsequent treatment followed practices previously described.

REFERENCES

1. Pohl, H. "Dielectrophoresis", Cambridge University Press, 1978.
2. Coster, H. G. L. and Zimmermann, U. "Direct Demonstration of Dielectric Breakdown in the Membranes of *Valonia utricularis.*" Zeitschrift für Naturforschung. 30 c, 77–79.1975.
3. Coster, H. G. L. and Zimmermann, U. "Dielectric Breakdown in the Membranes of *Valonia utricularis*: the role of energy dissipation". Biochimica et Biophysica Acta. 382, 410–418,1975.
4. Coster, H. G. L. and Zimmermann, U. "The mechanisms of Electrical Breakdown in the Membranes of *Valonia utricularis.*" Journal of Membrane Biology. 22, 73–90, 1975.
5. Zimmermann, U. "Electrical Field Mediated Fusion and Related Electrical Phenomena", Biochimica et Biophysica Acta. 694, 227–277. 1982.
6. Sale, J. H. and Hamilton, W. A. "Effects of High Electric Fields on Micro-Organisms", Biochimica et Biophysica Acta. 163, 37–43, 1968.
7. Sepersu, E. H., Kinosita, K. and Tsong, T. Y. "Reversible and Irreversible Modification of Erythrocyte Membrane Permeability by Electric Fields" Biochimica et Biophysica Acta. 812, 779–785, 1985.
8. Neumann, B et al. "Cell Fusion Induced by High Electrical Impulses Applied to Dictyostelium", Naturwissenschaften 67, 414, 1980

9. Zimmermann, U. et al "Fusion of *Avena Sativa* Mesophyll Proptoplasts by Electrical Breakdown", Biochimica et Biophysica Acta. 641, 160–165, 1981. 1982.

It will be recognised by persons skilled in the art that numerous variations and modifications may be made to the invention as described above without departing from the spirit or scope of the invention as broadly described.

We claim:

1. A method for the selective recovery of cells, vectors, particles or molecules expressing or presenting a defined ligand, comprising the steps of physically or chemically binding to a surface of a solid and immobile target a ligand or ligands complementary to the defined ligand, introducing the target into a suspension or solution of cells, vectors, particles or molecules in an electrically conductive liquid in which some of the cells, vectors, particles or molecules express or present the defined ligand, causing at least some of the cells, vectors, particles or molecules expressing or presenting the defined ligand to migrate into contact with the target and to bind with the complementary ligand or ligands by establishing between a pair of electrodes in the suspension or solution an alternating electric field of such a frequency, intensity and inhomogeneity that at least some of the cells, vectors, particles, ligands or molecules expressing or presenting the defined ligand will move towards the target, and separating the cells, vectors, particles or molecules which have bound to the target due to a dielectrophoretic force induced by the said alternating electric field from at least some of the other cells, vectors, particles or molecules in the suspension or solution.

2. A method as claimed in claim 1 in which the complementary ligand or ligands, is or are, attached to one of the electrodes which itself constitutes the target.

3. A method as claimed in claim 1 in which the at least one of the frequency and intensity and inhomogeneity of the electric field is altered after the cells, vectors, particles or molecules have become bound to the ligand or ligands on the target so as to cause at least some of the bound cells, vectors, particles or molecules to migrate away from the target.

4. A method as claimed in claim 1 in which vibration, stirring or other mechanical means is used to detach at least some of the bound cells, vectors, particles or molecules from the target.

5. A method as claimed in claim 1 in which the cells, vectors, particles or molecules which are bound to the target and the other cells, vectors, particles or molecules in the suspension or solution are separated by physically flushing unbound cells, vectors, particles or molecules away from the target or by removing the target from the vicinity of the unbound cells, vectors, particles or molecules.

6. A method as claimed in claim 1 in which in addition to the alternating electric field applied to the suspension or solution of cells, vectors, particles or molecules between the electrodes a direct current electric field is simultaneously applied to the cells, vectors, particles or molecules therein.

7. A method as claimed in claim 1 in which the ligand bound to the target is a chemical ligand which is not part of a cell or vector.

8. A method as claimed in claim 1 in which the ligand bound to the target is a part of a cell or vector.

9. A method as claimed in claim 1 in which the method is used for the separation of cells.

10. A method as claimed in claim 2 in which the complementary ligand or ligands, is or are bound to an electrode by non-specific binding of the ligand or ligands to the electrode induced by the application of an electric field between the electrodes in the solution or suspension containing the ligand.

11. A method as claimed in claim 10 in which the electric field is an alternating electric field and a direct current electric field in combination so selected that the ligands will be deposited on the other electrode in a variety of orientations.

12. A method for the separation of cells, vectors, particles or molecules in a suspension or solution of cells, vectors, particles or molecules of at least two different species thereof in an electrically conductive liquid, comprising the steps of establishing between two electrodes in the liquid an alternating electric field of such frequency, intensity and inhomogeneity as to selectively cause the cells, vectors, particles or molecules of one specie to migrate through the liquid towards the electrodes due to a dielectrophoretic force induced by the said alternating electric field while simultaneously or sequentially causing the cells vectors, particles or molecules of the other specie to migrate through the liquid away from the electrodes due to a dielectrophoretic force induced by the said alternating electric field and separating the cells, vectors, particles or molecules which have migrated towards the electrodes from the cells, vectors, particles or molecules that have migrated away from them the electrodes.

13. A method as claimed in claim 12 in which the alternating electric field is maintained until some or all of the cells, vectors, particles or molecules of the one specie is in contact with at least one of the electrodes and remaining cells, vectors, particles or molecules are then separated from the cells, vectors, particles, or molecules in contact with the electrode or electrodes.

14. A method as claimed in claim 13 in which a surface of at least one of the electrodes carries a ligand or ligands to which cells, vectors, particles or molecules of the one specie will bind specifically.

15. A method as claimed in claim 13 in which the alternating electric field is such that the cells, vectors, particles or molecules of the one specie is caused to migrate through the liquid towards the electrodes while simultaneously the cells, vectors, particles or molecules of the other specie migrates away from the electrodes.

16. A method as claimed in claim 13 in which the method is applied for the separation of cells of at least two species.

17. A method for fusing a selected first cell with a selected second cell to form a single fusate cell, comprising the steps of:

i) physically or chemically binding at least one first cell to a first of a pair of electrodes between which an alternating electric current of an appropriate frequency, intensity and inhomogenicity subsists such that each first cell is drawn into direct contact with one of the electrodes, the physical or chemical binding being so achieved that when a plurality of fusate cell are formed there is only a monolayer of cells present on said one of the electrodes;

ii) physically manipulating a single second cell into sufficiently close proximity with the first cell or one of the first cells such that the second cell is drawn into juxtaposition with the said first cell by a local dielectrophoretic field of the said first cell induced by the alternating electric current between the electrodes; and iii) causing the first and second cells to fuse.

18. A method as claimed in claim 17 in which said single second cell is physically or chemically bound to a second of the pair of electrodes and is then brought into proximity with the said first cell by physical manipulation of one of the electrodes.

19. A method as claimed in claim 18 in which the first and second cells are released from at least one of the electrodes before they are fused.

20. A method as claimed in claim 19 in which the first and second cells are released from both of the electrodes before they are fused.

21. A method as claimed in claim 17 in which the juxtaposed cells are fused by a fusagenic agent selected from the group comprising application of an intense electric field, a fusagenic chemical, viral mediation and a combination of at least two of the foregoing.

22. A method as claimed in claim 18 in which said second cell is attached to the second electrode, another second cell is attached to the second cell already attached to the second electrode and this other second cell is released from the second electrode in close proximity to the first cell by changing the alternating electric field so that the other second cell is separated from the second electrode, withdrawing the second electrode from proximity with the other second cell and again changing the alternating electric field so that the other second cell is caused to move into juxtaposition with the first cell.

23. A method as claimed in claim 22 in which the electric field is changed so that the other second cell on the second electrode is repelled from the second cell on the second electrode, without necessarily withdrawing the second electrode, towards the first cell on the first electrode, and then changing the electric field when the other second cell has reached a position between the two electrodes, so that the other second cell is moved into juxtaposition with the first cell.

24. A method as claimed in claim 17 in which one of the first and the second cell is replaced by a vector.

* * * * *